(12) United States Patent
Wever et al.

(10) Patent No.: US 9,103,833 B2
(45) Date of Patent: Aug. 11, 2015

(54) USE OF THE GTPASE RAB27B TO DIAGNOSE AND TREAT POOR PROGNOSIS ESTROGEN-RECEPTOR-POSITIVE BREAST CANCER

(75) Inventors: Olivier De Wever, Oostende (BE); An Hendrix, Mol (BE); Wendy Westbroek, Rockville, MD (US)

(73) Assignee: Universiteit Gent, Ghent (BE)

( * ) Notice: Subject to any disclaimer, the term of this patent is extended or adjusted under 35 U.S.C. 154(b) by 349 days.

(21) Appl. No.: 13/320,729

(22) PCT Filed: May 12, 2010

(86) PCT No.: PCT/EP2010/056542
§ 371 (c)(1),
(2), (4) Date: Nov. 15, 2011

(87) PCT Pub. No.: WO2010/130782
PCT Pub. Date: Nov. 18, 2010

(65) Prior Publication Data
US 2012/0065147 A1 Mar. 15, 2012

(30) Foreign Application Priority Data
May 15, 2009 (GB) .................................. 0908467.4

(51) Int. Cl.
| | |
|---|---|
| *A61K 48/00* | (2006.01) |
| *C12Q 1/68* | (2006.01) |
| *G01N 33/574* | (2006.01) |
| *C07K 14/82* | (2006.01) |
| *C12N 15/113* | (2010.01) |

(52) U.S. Cl.
CPC .......... *G01N 33/57415* (2013.01); *C07K 14/82* (2013.01); *C12N 15/1135* (2013.01); *C12N 2310/14* (2013.01); *G01N 2333/4719* (2013.01)

(58) Field of Classification Search
None
See application file for complete search history.

(56) References Cited

U.S. PATENT DOCUMENTS

2005/0255487 A1* 11/2005 Khvorova et al. ................. 435/6
2007/0218512 A1 9/2007 Strongin et al.

FOREIGN PATENT DOCUMENTS

| WO | WO 03004989 A2 * | 1/2003 |
|---|---|---|
| WO | WO 2004/111603 | 12/2004 |
| WO | WO 2010/130782 | 11/2010 |

OTHER PUBLICATIONS

Fisher et al, Relative Worth of Estrogen or Progesterone Receptor and Pathologic Characteristics of Differentiation as Indicators of Prognosis in Node Negative Breast Cancer Patients: Findings From National Surgical Adjuvant Breast and Bowel Project Protocol B-06, 1988, Journal of Clinical Oncology, vol. 6, 7:1076-1087.*
Caldas et al.; The Molecular Outlook; Nature; vol. 415, Jan. 31, 2002; pp. 484485.
Hendrix et al.; Effect of the secretory small DTPase Rab27B on breast cancer growth, invasion, and meastasis; Journal of the National Cancer Institute; Jun. 16, 2010; vol. 102, No. 12; pp. 866880.
Hendrix et al.; New Insights in the Link between Rab27b GTPase and Breast Cancer; Molecular Biology of the Cell; vol. 17, No. Suppl. S. 2006; pp. 1059-1524.
International Search Report PCT/EP2010/056542 dated Sep. 27, 2010.
Wright et al.; Estrogen regulates vesicle trafficking gene expession in EFF-3, EFM-19 and MCF-7 breast cancer cells; International Journal of Clinical and Experimental Pathology 2009; vol. 2, No. 5; Jan. 30, 2009; pp. 463475.
International Preliminary Report on Patentability; PCT/EP2010/03542 dated Nov. 15, 2011.
Dunnwald et al., Hormone receptor status, tumor characteristics, and prognosis: a prospective cohort of breast cancer patients, Breast Cancer Research, 2007, pp. 1-10, vol. 9, No. 1.
Pagani et al., Patterns of recurrence of early breast cancer according to estrogen receptor status: a therapeutic target for a quarter of a century, Breast Cancer Res. Treat., 2009, pp. 319-324, vol. 117.

* cited by examiner

*Primary Examiner* — Tracy Vivlemore
*Assistant Examiner* — Kate Poliakova
(74) *Attorney, Agent, or Firm* — TraskBritt, P.C.

(57) ABSTRACT

The present invention relates to evaluating the prognosis of patients with estrogen receptor-positive breast cancer on the basis of Rab27B expression. The invention further relates to a kit comprising an assay for measuring Rab27B levels in said patients and to the usage of Rab27B as a target to screen for drugs capable of inhibiting or diminishing metastasis of said cancer. Furthermore, the invention discloses compounds which can be used to treat estrogen receptor-positive breast cancer.

11 Claims, 10 Drawing Sheets

SEQUENCE LISTING

<160> NUMBER OF SEQ ID NOS: 7

<210> SEQ ID NO 1
<211> LENGTH: 21
<212> TYPE: DNA
<213> ORGANISM: Homo sapiens

<400> SEQUENCE: 1
aaacgtgtgg tttataatgc a               21

<210> SEQ ID NO 2
<211> LENGTH: 21
<212> TYPE: DNA
<213> ORGANISM: Homo sapiens

<400> SEQUENCE: 2
taggaataga ctttcgggaa a               21

<210> SEQ ID NO 3
<211> LENGTH: 15
<212> TYPE: PRT
<213> ORGANISM: Homo sapiens

<400> SEQUENCE: 3

Val Gly Ile Asp Phe Arg Glu Lys Arg Val Val Tyr Asn Ala Gln
1               5                   10                  15

<210> SEQ ID NO 4
<211> LENGTH: 15
<212> TYPE: PRT
<213> ORGANISM: Homo sapiens

<400> SEQUENCE: 4

Ala Gln Gly Pro Asn Gly Ser Ser Gly Lys Ala Phe Lys Val His
1               5                   10                  15

<210> SEQ ID NO 5
<211> LENGTH: 15

```
<212> TYPE: PRT
<213> ORGANISM: Homo sapiens

<400> SEQUENCE: 5

Glu Arg Phe Arg Ser Leu Thr Thr Ala Phe Phe Arg Asp Ala Met
1               5                   10                  15

<210> SEQ ID NO 6
<211> LENGTH: 15
<212> TYPE: PRT
<213> ORGANISM: Homo sapiens

<400> SEQUENCE: 6

Gly Asn Ser Gly Asn Leu Asp Gly Glu Lys Pro Pro Glu Lys Lys
1               5                   10                  15

<210> SEQ ID NO 7
<211> LENGTH: 11
<212> TYPE: PRT
<213> ORGANISM: Homo sapiens

<400> SEQUENCE: 7

Asp Gln Val Ala Asn Ser Ala Phe Val Glu Arg
1               5                   10
```

USE OF THE GTPASE RAB27B TO DIAGNOSE AND TREAT POOR PROGNOSIS ESTROGEN-RECEPTOR-POSITIVE BREAST CANCER

CROSS-REFERENCE TO RELATED APPLICATIONS

This is a national phase entry under 35 U.S. §371 of international Patent Application PCT/EP2010/056542, filed May 12, 2010, published in English as International Patent Publication WO 2010/130782 A1 on Nov. 18, 2010, which claims the benefit under Article 8 of the Patent Cooperation Treaty to United Kingdom Patent Application Serial No. 0908467.4, filed May 15, 2009.

TECHNICAL FIELD OF THE INVENTION

The present invention relates to evaluating the prognosis of patients with estrogen receptor-positive breast cancer on the basis of Rab27B expression. The invention further relates to a kit comprising an assay for measuring Rab27B levels in said patients and to the usage of Rab27B as a target to screen for drugs capable of inhibiting or diminishing metastasis of said cancer. Furthermore, the invention discloses compounds which can be used to treat Rab27B-positive poor prognosis estrogen receptor-positive breast cancer.

BACKGROUND ART

Cancers achieve invasive growth by delivering critical factors into the tumor microenvironment (1), but the molecular mechanisms for the secretion of these pro-invasive factors remain largely unknown. One likely process involves vesicle exocytosis, whose role in tumor progression was first reported by Palmer and co-workers (2). They showed that ectopic expression of BAIAP3, a Munc 13-like effector of regulated exocytosis, enhanced the malignancy of cancer cells.

Key players in exocytic and endocytic membrane trafficking include the Rab GTPases, which serve as molecular switches oscillating between their GTP-bound active and GDP-bound inactive conformations. Rabs recruit specific protein complexes to elicit their biological functions (3-6); they are post-translationally modified by geranylgeranylation, which binds them to lipophilic membranes (7).

The secretory pathway can be divided into constitutive and regulated portions (8). In the constitutive pathway, release of vesicle content occurs at a constant rate, and vesicles do not accumulate to an appreciable extent (9). In contrast, regulated secretion involves two distinct steps. Newly synthesized proteins are first stored within vesicular structures and are then released upon stimulation (10). Certain Rab GTPases, referred to as secretory Rabs, control this secretory process; they include Rab26, Rab37, Rab3A/B/C/D, and Rab27A/B (11). Rab26 and Rab37 are thought to modulate secretion in specialized cell types, whereas the Rab3 and Rab27 subfamilies function as more generic regulators of secretion (12-16). The Rab27 subfamily has the highest homology (41-44%) to members of the Rab3 subfamily; Rab27A and Rab27B exhibit 71% identity at the amino acid level (17).

Rab proteins of the endocytic (e.g., Rab25, Rab23 and Rab5) (18-21) and constitutive secretory pathways (e.g. Rab8) (22) play significant roles in malignancy and Rab GTPases active in exocytosis/secretion could also be critical for cancer progression.

WO 2006/091776 discloses a method for predicting prostate cancer progression via determining the expression level of a set of genes such as the gene encoding for Rab27. WO 03/004989 further discloses that Rab27B is over-expressed in breast cancer cells and that Rab27B can be used to screen for the presence of breast cancer. Hendrix et al. (40) further indicates that Rab27B is a potential biomarker in breast cancer progression. US 2007/0218512 indicates that human matrix metalloproteinase 26 (MMP 26) can be used as a biomarker, possibly in combination with an additional biomarker such as Rab27B, for evaluating the prognosis of cancers, among them ER-positive breast cancers. Recently, Wang and co-workers showed that up-regulation of Rab27A further enhances the already established invasive and metastatic phenotypes of the human breast cancer cell lines MDA-MB-231 and MDA-MB-435 (23, 36). In these models, Rab27A had a peri-nuclear and non-cytoskeleton associated localization pattern, suggesting a non-secretory function of Rab27A in MDA-MB cell lines. Human Rab27A and B are further structurally very similar and are functional homologues with respect to melanosome transport (35).

ER positive breast cancers, which comprise the majority of breast malignancies, carry a better prognosis for disease-free survival and overall survival than ER-negative breast cancers (37). Nevertheless, some ER-positive breast cancers are more invasive and tend to metastasize more frequently than other ER-positive tumors. A low degree of differentiation and the presence of metastasis in the axillary lymph nodes are typical characteristics. The underlying reasons for the more aggressive character are poorly understood. In this regard, Wright et al. (41) recently demonstrate in FIG. 3 of their publication that a lower level of Rab27B expression was found in ER-negative breast cancer tissue samples compared to the Rab27B expression in ER-positive samples which suggests that relatively increased Rab27B expression correlates with a positive outcome of disease.

However, it is currently still unknown which biomarker can be used to evaluate the prognosis of patients with estrogen receptor-positive breast cancer and especially the subset of patients with ER-positive breast cancers which are more invasive and tend to metastasize more frequently, or, can be used as target for drugs to treat the latter subset of patients.

Thus, needed in the art are reliable methods for stratifying, prognosing and treating the ER-positive breast cancers which are more invasive and tend to metastasize more frequently than other ER-positive tumors, as well as predicting treatment outcomes.

ions containing the C-terminal fragment are known as 'y' ions, whereas ions containing the N-terminal fragment are known as 'b' ions. The search engine Mascot uses this information to report probability-based scores for each peptide. See Methods for more details. B) Quantification of HSP90α levels in conditioned media (CM) of GFP- vs GFP-Rab27B—expressing MCF-7 cells using enzyme-linked immunosorbent assay ELISA. Results are means with upper 95% confidence intervals of two independent experiments with three replicates. C) Western blot analysis of HSP90α and β in CM (upper panel) and in total protein lysates (lower panel) of transfected MCF-7 cells. Relative intensity was quantified with HSP90β or tubulin as a loading control. D) Impact of Rab27B silencing (siRab27B 1 and 2) versus control silencing (siCON) on the expression of GFP-Rab27B protein (lower panel) and secretion of HSP90α and β (upper panel) in the CM of MCF-7 GFP-Rab27B cells. Protein levels were quantified as immunostaining intensity relative to tubulin and HSP90β respectively.

Figure 5:
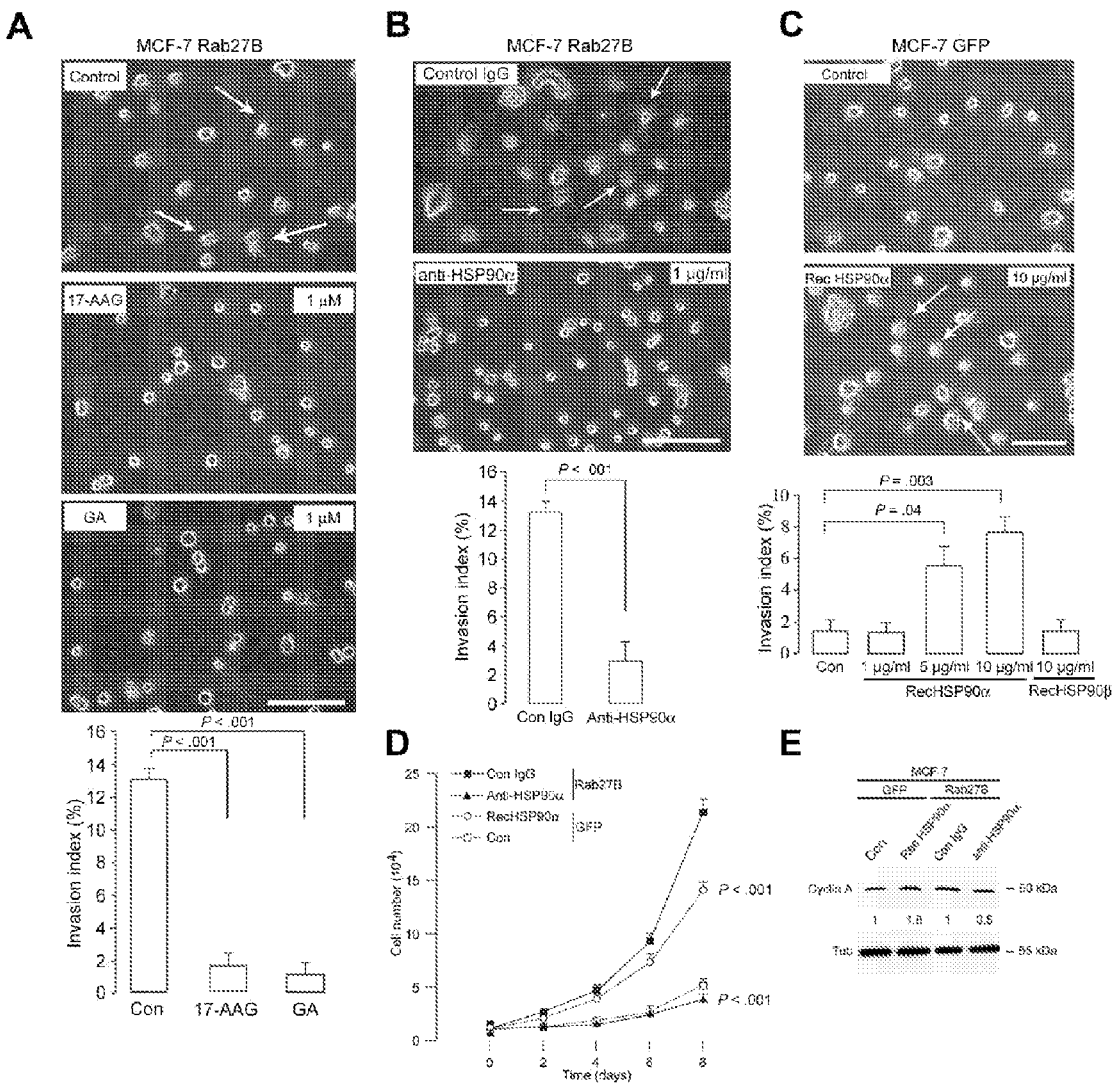
Figure 5:
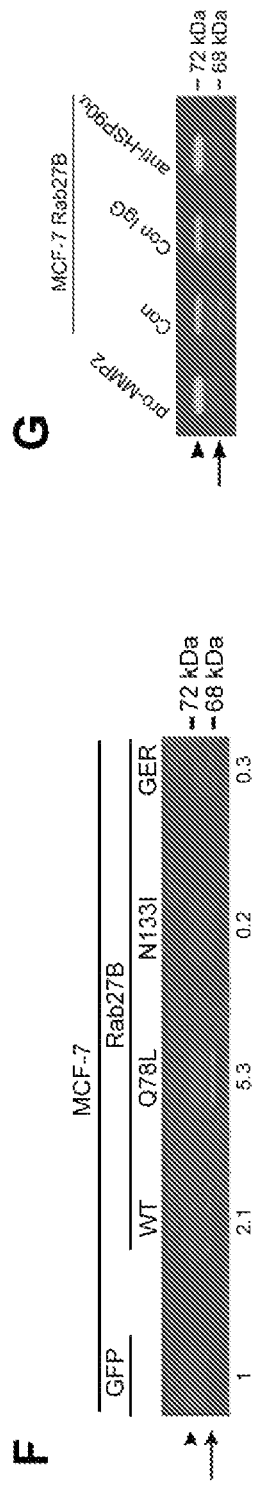

FIG. 5. The role of HSP90α and MMP-2 in Rab27B-dependent invasion. A) Phase contrast images showing morphology (upper panels) and quantification of collagen type I invasion by MCF-7 GFP-Rab27B cells (lower panel) treated with the HSP90α inhibitors 17-AAG and GA (1 μM) for 24 hours or left untreated (Control, Con). B) Morphology (upper panels) and quantification (lower panel) of the invasive phenotype induced by GFP-Rab27B in MCF-7 cells cultured on collagen type I matrix treated for 6 hours with HSP90α-neutralizing antibody (1 μg/mL) or the control IgG isotype. C) Morphology (upper panel) and quantification (lower panel) of the invasive phenotype induced by GFP-Rab27B in MCF-7 cells cultured on collagen type I matrix and treated for 24 hours in the presence or absence (Control, Con) of recombinant (rec) HSP90α protein (1, 5 and 10 μg/mL) or recombinant HSP90β protein (10 μg/mL). In A, B and C, arrows indicate cellular extensions and local spreading. Scale bar, 100 μm. Invasion indices are means and upper 95% confidence intervals derived from the means of three independent experiments performed in triplicate. P-values are calculated using the $\chi^2$-test; statistically significant P-values are indicated. D) Measurement of cell proliferation rates of MCF-7 GFP cells treated with recombinant HSP90α (10 μg/mL) or left untreated (Con) and of MCF-7 GFP-Rab27B cells challenged with a HSP90α-neutralizing antibody (5 μg/mL) or control immunoglobulin (Con IgG). Proliferation assay was performed as in FIG. 2,G. Mean number of cells is plotted with upper 95% confidence intervals. P-values are calculated using the two-way repeated measures ANOVA test. E) Cyclin A expression was evaluated in MCF-7 GFP cells treated with recombinant HSP90α (10 μg/mL) or left untreated (Con) and in MCF-7 GFP-Rab27B cells challenged with HSP90α-neutralizing or control antibody. Intensity was quantified relative to tubulin. F) Analysis of MMP-2 activity in conditioned media (CM) from cultured MCF-7 cells expressing GFP, GFP-Rab27B (wild type, WT), or the GFP-Rab27B mutants (Q78L, N133I, and GER) by gelatin zymography. G) Gelatin zymography of MMP-2 activity in CM from MCF-7 GFP-Rab27B cells that were pre-incubated with exogenously added proMMP-2 (100 ng/mL) in serum-free medium for 24 hours. In F and G, arrowhead indicates 72 kDa proMMP-2 and arrow indicates 68 kDa active protease.

Figure 6:
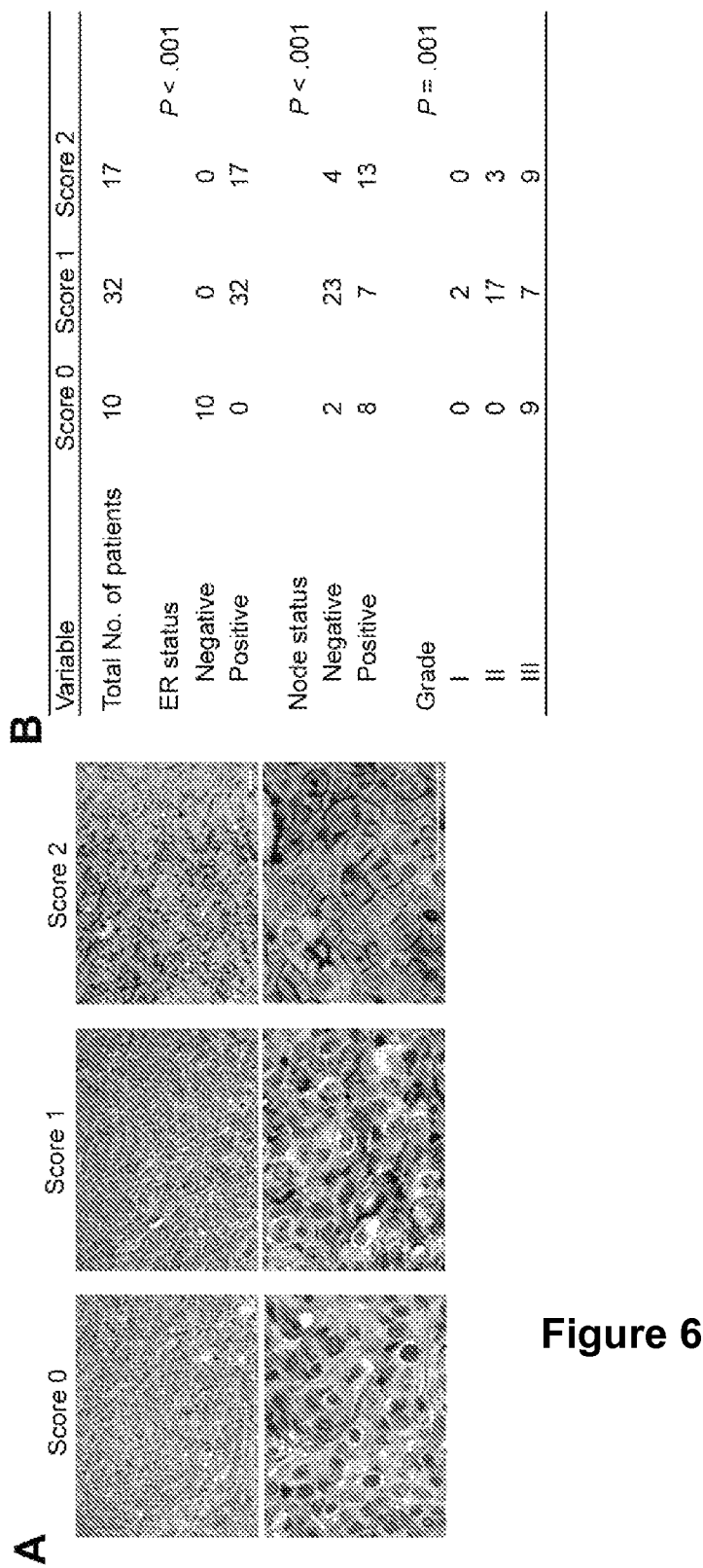
Figure 6:
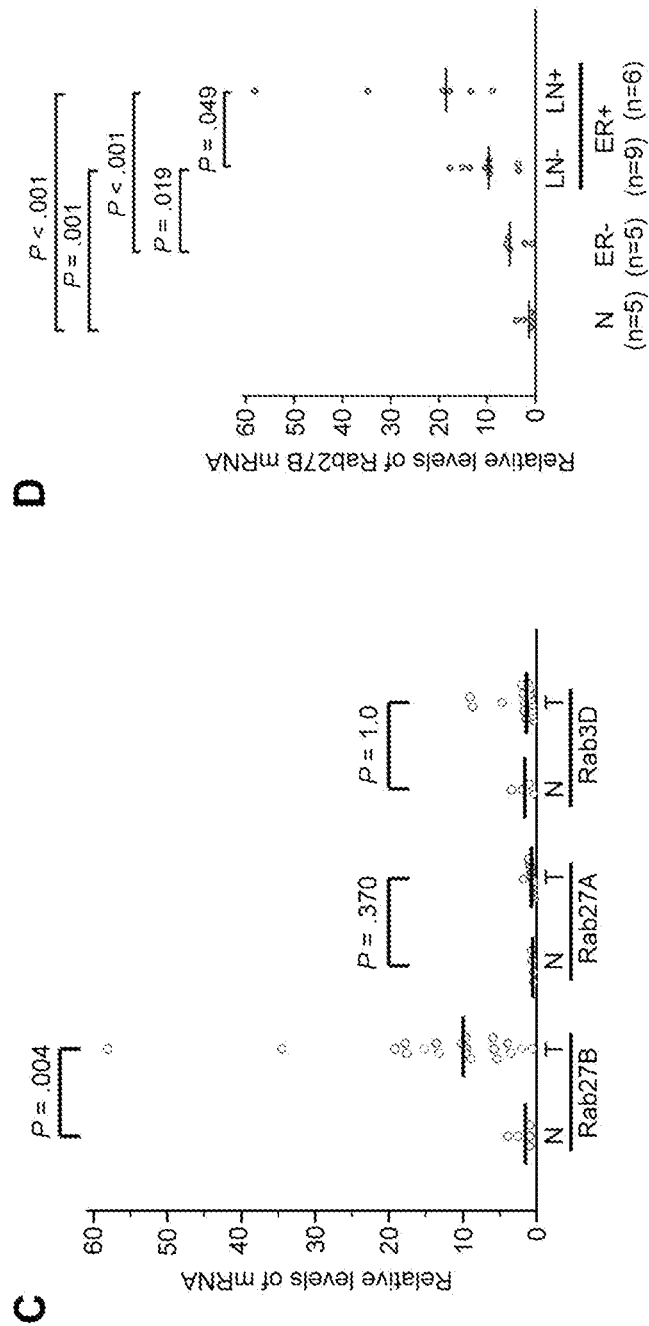

FIG. 6. Rab27B expression in clinical breast cancer specimens. A) Representative Rab27B stained primary breast cancer samples that illustrate immunohistochemical scores of 0, 1, and 2. Scale bar, 100 μm. B) Associations of Rab27B immunohistochemical scores with estrogen receptor (ER) status and other clinicopathological data for 59 primary breast tumors. The $\chi^2$-test was used to test for differences between categorical variables. C) Relative levels of Rab3D, Rab27A, and Rab27B mRNA expression in normal tissue (N, n=5) versus primary breast carcinoma (T, n=20). D) Expression of Rab27B mRNA in 5 normal tissues versus 20 primary breast carcinomas. Tumor samples were divided into three groups according to ER status and lymph node (LN) involvement. In C) and D) mRNA expression was measured by quantitative RT-PCR in triplicate. Horizontal bars represent median for each group (two-sided Mann-Whitney test).

DESCRIPTION OF THE INVENTION

The present invention relates to the surprising finding that one particular secretory rat brain (Rab) protein, Rab27B, promotes cancer cell invasion, tumor growth and metastasis. Rab27A, which is structurally very similar to Rab27B, does not have such an effect. Further surprising is the fact that, in clinical samples, upregulation of endogenous levels of Rab27B mRNA and protein correlates with lymph node metastasis and differentiation grade in ER-positive breast tumors. In contrast, the recent data by Wright et al. (41) suggested that increased Rab27B expression correlates with a positive outcome of disease.

Hence, the present invention relates to the use of the guanosine triphosphate hydrolaze (GTPase) Rat brain (Rab) 27B as a biomarker to evaluate the prognosis of a patient with estrogen receptor-positive breast cancer in vitro. With the term 'biomarker' is meant a characteristic that is objectively measured and evaluated as an indicator of normal biologic processes, pathogenic processes, or pharmacologic responses to a therapeutic intervention. Hence, the biomarker Rab27B can be used, among other uses, to: 1) diagnose estrogen receptor-positive breast cancer with the potential to metastasize and/or to develop in a grade 3 tumor (see further); 2) evaluate the prognosis of said breast cancer which encompasses predictions about the likely course of disease or disease progression, particularly with respect to the likelihood of metastasis, disease remission, disease relapse, tumor recurrence and death; 3) therapeutically stratify patients with estrogen receptor-positive breast cancer (i.e. scoring said patients, see further) in order to decide which therapy, such as (adjuvant) chemotherapy, should be given to said patient; and 4) monitor disease progression once a particular therapy has been administered to said patients.

In particular, the present invention relates to the latter usage, wherein an increased level of Rab27B in a patient sample, compared to a control sample, indicates a poor prognosis. The term 'a patient sample' includes, but is not limited to, a primary tumor sample, circulating breast cancer cells or a biofluid such as blood, serum, plasma lymph, urine, saliva, nipple aspirates, gynecological fluids or any other bodily secretion or derivative thereof. In this regard, it should be noted that Rab27B protein can be detected intracellularly (often as part of a membrane), or, extracellularly as a secreted form or as part of a secreted vesicle (i.e. as part of the so-called exosome). Methods for collecting various samples are well known in the art. In some embodiments, a breast tissue sample is obtained by, for example, fine needle aspiration biopsy, core needle biopsy or excisional biopsy. The term 'poor prognosis' corresponds with positive lymph node metastasis and/or a poor differentiation grade. The term 'a poor differentiation grade' refers to the so-called 'Bloom-Richardson grade' (BR grade, (38)) which is a histological grade assigned by pathologists to invasive breast cancers and is the most common type of cancer grade system currently used. It is a semi-quantitative grading method based on three morphologic features of invasive breast cancers. The morphologic features that are used are:

1. The degree of tumor tubule formation (percentage cancer composed of tubular structures)
2. The mitotic activity of the tumor (rate of cell division)
3. The nuclear pleomorphism of tumor cells (nuclear grade, change in cell size and uniformity)

Each of these features is assigned a score ranging from 1 to 3. The scores are then added together for a final sum that will range between 3 and 9. This value is then used to grade the tumor as follows:

Grade 1 (I) tumor (well-differentiated)
Grade 2 (II) tumor (moderately-differentiated)
Grade 3 (III) tumor (poorly-differentiated)

The terms 'an increased level of Rab27B in a patient sample, compared to a control sample' depends on which level of Rab27B is measured and how this level is measured. With a 'control sample' is meant a similar sample as indicated above taken from a healthy patient not having estrogen receptor-positive breast cancer and/or a patient having estrogen receptor-positive breast cancer but without lymph node metastasis. In a particular embodiment, the present invention relates to the latter usages wherein the level of Rab27B is determined by measuring the expression of Rab27B protein or nucleic acids such as mRNA expression of Rab27B. Measuring proteins and nucleic acid levels (such as mRNA levels) are well known in the art and can be undertaken by any method known in the art including but not limited to Western blots, Northern blots, Southern blots, ELISA, immunoprecipitation, immunofluorescense, flow cytometry, Rab27B activation test (i.e. GTP vs GDP-bound Rab27B), immunohistochemistry, nucleic acid hybridization techniques, nucleic acid reverse transcription methods, and nucleic acid amplification methods such as qPCR. The latter techniques are, for example, described in detail in US 2007/0218512. In particular embodiments, expression of a biomarker is detected on a protein level using antibodies that are directed against specific biomarker proteins. These antibodies can be used in various methods such as Western blot, ELISA, immunoprecipitation or immunohistochemistry. Likewise, immunostaining of breast tumor tissue can be combined with assessment of clinical information, conventional prognostic methods, and expression of other molecular markers known in the art.

With regard to 'increased levels of Rab27B protein compared to a control', the present invention further relates in particular to any of the latter usages, wherein more than 30% of cancer cells of a sample taken from a patient show Rab27B protein membrane localization and/or vesicle clustering. The Rab27B protein signal was scored on the following scale:

score 0: no or weak cytoplasmic staining and less than 5% (5% not included) of cancer cells with membrane localization or vesicle clustering, score 1: cytoplasmic staining and between 5% and 30% of the cancer cells with prominent membrane localization and vesicle clustering, score 2: cytoplasmic staining and more than (>) 30% (30% not included) of the cancer cells with prominent membrane localization and vesicle clustering.

In this regard, the present invention discloses a statistically significant, positive correlation between Rab27B protein score 2, positive lymph node metastasis and a higher tumor grade, such as grades II and III (i.e. grades 2 and 3).

The present invention further relates to the latter usages, wherein the level of mRNA expression of Rab27B is higher in a patient with lymph node metastasis compared with a patient without lymph node metastasis. For example, the present invention discloses that the median expression of Rab27B was two-fold higher in the estrogen-positive patients with lymph node metastasis compared with those without lymph node metastasis and was 11-fold higher compared to normal tissue. The term 'higher' in relation to nucleic acid levels such as mRNA levels thus refers to at least 1.1, 1.2, 1.3 . . . 2, 2.1, 2.2, 2.2, 3, 4, . . . 10, 11, 12, 122.1, 12.2, 12.3 . . . -fold 'higher' levels compared to the levels determined in a control sample.

The present invention also relates to a kit comprising reagents to perform an assay for measuring Rab27B levels in a patient having estrogen receptor-positive breast cancer in vitro in order to determine if said patient is at risk to develop lymph node metastasis. The term 'kit' refers to any manufacture (e.g. a package or a container) comprising at least one reagent (e.g. an antibody, a nucleic acid probe, etc.) for performing and assay which specifically detects the expression of Rab27B. Positive and/or negative controls can be included in the kits to validate the activity and correct usage of reagents employed in accordance with the present invention. The design and use of controls is standard and well within the routine capabilities of those of ordinary skill in the art. The kit can be promoted, distributed, or sold as a unit for performing the methods or usages of the present invention. Additionally, the kits can contain a package insert describing the kit and methods/usages for its use.

Preferred assays to perform via the kit are a Rab27B immunohistochemistry assay or Quantitative RT-PCR assay on tissues or cells such as biopsies, primary breast cancer samples or circulating breast cancer cells of the patients, or, a sandwich-type ELISA on bio-fluids of primary breast cancer samples of the patients.

The present invention also relates to the use of Rab27B as a target to screen for drugs capable of inhibiting or diminishing metastasis of estrogen receptor-positive breast cancer in a patient. Screening assays are well-known in the art and are, for example, described in detail in WO 03/004989 and WO 2006/091776. The latter assays aim to identify modulators (antibodies, peptides, peptidomimetics, small molecules, nucleic acids or other drugs) which: a) bind to Rab27B, b) have a modulatory (i.e. stimulatory or inhibitory) effect on the activity of Rab27B, c) have a modulatory effect on the interactions of said biomarkers with one or more of their substrates or binding partners, or d) have a modulatory effect on the expression of said biomarkers. Such assays typically comprise a reaction between Rab27B or nucleic acids encoding said protein, and, the modulators or test compounds. Said test compounds (or modulators or drugs) may be obtained from any available source, including libraries of natural and/or synthetic compounds. The screening methods of the invention will provide 'hits' or 'leads' that possess a desired but not optimized biological activity. Lead optimization performed on these compounds to fulfill all physicochemical, pharmacokinetic and toxicological factors required for clinical usefulness may provide improved drug candidates. It should be noted that in the latter screening assays also fragments or variants of Rab27B or the corresponding encoding nucleic acids can be used as long as these fragments or variants will provide hits or leads that possess the desired biological activity. A fragment is a shorter portion of Rab27B or of their encoding nucleic acids. A variant encodes for or has an amino acid sequence that has at least 70% or 75% sequence identity, preferably at least 80% or 85% sequence identity and more preferably at least 90%, 91%, 92%, 93%, 94%, 95%, 96%, 97%, 98% or 99% sequence identity with Rab27B.

The present invention further relates to compounds capable of interfering with the mRNA expression of Rab27B or the biological activity of Rab27B protein for use to treat progression of estrogen receptor-positive breast cancer in a patient. Said compounds include antibodies such as camelantibodies or nanobodies (Van Impe et al (51); Delanote et al. (45)), peptides such as the so-called Trojan peptides (Gratton et al (47)) or Alpha bodies (www.complix.be), peptidomimetics, small molecules, nucleic acids or any other drug as indicated above.

The present invention particularly relates to a compound capable of interfering with the mRNA expression of Rab27B or the biological activity of Rab27B protein for use to treat progression of estrogen receptor-positive breast cancer in a patient wherein said compound is chosen from the list consisting of: 1) a Rab27B-specific small interfering RNA molecule(siRNA) as the present invention demonstrates that targeting of Rab27B by single or pooled siRNA's depletes Rab27B protein and is accompanied by loss of the invasive phenotype of human breast cancer cells, 2) a peptide targeting a functional domain of Rab27B or a peptide targeting a Rab27B-specific domain, or, 3) a small molecule inhibiting the enzymatic activity of geranylgeranyltransferases as described by Lackner et al. (39).

More particularly, the present invention relates to a) Rab27B-specific small interfering RNA molecules which target or bind to the Rab27B nucleic acid sequences 5'AAACGTGTGGTTTATAATGCA3' (SEQ ID NO:1) or 5'TAGGAATAGACTTTCGGGAAA3' (SEQ ID NO:2), b) peptides targeting or binding to the Rab27B functional amino acid domains VGIDFREKRVVYNAQ (SEQ ID NO:3) (which corresponds to the amino acid positions 42-56 of Rab27B protein), AQGPNGSSGKAFKVH (SEQ ID NO:4) (amino acid region 55-69) or ERFRSLTTAFFRDAM (SEQ ID NO:5) (amino acid region 79-93), or, c) peptides targeting or binding to the Rab27B-specific 15 amino acid C-terminal tail consisting of the amino acids GNSGNLDGEKPPEKK (SEQ ID NO:6).

By the term 'treatment' is meant the medical management of a patient with the intent to cure, ameliorate, stabilize, or prevent a disease. It is further understood that appropriate doses of said compounds (which can also be denominated as drugs or pharmaceutical compositions) depends upon a number of factors within the knowledge of the ordinary skilled physician. The dose of these compounds will vary, for example, depending upon the identity, size, and condition of the patient being treated, upon the route of administration of said compounds (i.e. parenteral (intravenous, intradermal, subcutaneous), oral, transdermal, transmucosal or rectal) and upon the effect which the skilled physician desires the compound to have. A pharmaceutical composition is formulated to be compatible with its intended route of administration. Suitable diluents, solvents, antioxidants, chelating agents, buffers, carriers, isotonic agents, binding agents, adjuvants, flavoring agents, propellants, detergents and the like are described in detail in, for example, WO 03/004989.

The following non-limitative examples are given in order to further illustrate the present invention.

EXAMPLES

1. Rab27B as a Biomarker to Monitor Disease Progression
Materials and Methods
Cell Lines, Expression Vectors and Transfections Three ER-positive, non-invasive, and non-metastatic human breast cancer cell lines, MCF-7, T47D, and ZR75.1 (23) (ATCC, Manassas, Va.), were maintained in Dulbecco's Minimal Essential Medium supplemented with 10% fetal bovine serum, 100 U/mL penicillin, and 100 μg/mL streptomycin (Invitrogen, Carlsbad, Calif.). To prepare serum-free conditioned medium (CM), $2\times10^7$ cells per flask of each cell type were washed three times and incubated for 24 hours at 37° C. with 15 mL serum-free culture medium. The medium was harvested, centrifuged at 1,250 g for 5 minutes at 4° C., and passed through a 0.22 μm filter. CM was 30× concentrated at 4° C. in centriprep tubes YM-10 (Millipore, Billerica, Mass.).

To generate cells that expressed green fluorescent protein (GFP)-Rab fusion proteins, Rab3D, Rab27A, and Rab27B cDNAs were fused in-frame to GFP into the peGFP-C1 vector (Clontech, Mountain View, Calif.) and confirmed by sequencing. The source of Rab27B and Rab27A cDNA and GFP fusion constructs were described previously (34, 35); the Rab3D cDNA was purchased from Origene Inc. (Rockville, Md.). Mutant forms of Rab27B that encoded the T23N, N133I, and Q78L proteins and a geranylgeranyl-binding mutant (GER) were generated by PCR site-directed mutagenesis (Retrogen Inc., San Diego, Calif.). Breast cancer cell lines MCF-7, T47D, and ZR75.1 that stably or transiently overexpressed GFP-Rab fusion proteins were then generated by electroporation using the Cell Line Nucleofector Kit V according to the manufacturer's protocol (Amaxa, Gaithersburg, Md.). To establish stable cell lines, transfected cells were selected in G418 (1 mg/mL) (Invitrogen) for 4 weeks. At least four clones of each cell line were used for in vitro experiments to exclude clonal variation. Animal experiments were performed with one representative clone except for wild type (WT) GFP-Rab27B cells, of which four clones were tested.

Rab27B-specific HiPerformance guaranteed siRNAs (siRab27B-1 target=5' AAA CGT GTG GTT TAT AAT GCA 3' and siRab27B-2 target=5' TAG GAA TAG ACT TTC GGG AAA 3') and a scrambled RNAi negative control were purchased from Qiagen (Venlo, Netherlands). RNAi transfections were performed by electroporation using the Cell Line Nucleofector Kit V according to the manufacturer's protocol (Amaxa).

Antibodies and Reagents

The following primary antibodies were used for Western blot analysis or immunohistochemistry: mouse monoclonal anti-GFP (1:1000) (MAB3580; Millipore), mouse monoclonal anti-tubulin (1:1000) (T5168; Sigma-Aldrich, St Louis, Mo.), rabbit polyclonal anti-Rab27B (1:1000) (24), mouse monoclonal anti-cyclin E (1:500) (AHF0312; Invitrogen), mouse monoclonal anti-cyclin A (1:250) (33-4900; Zymed Laboratories, San Francisco, Calif.), rabbit monoclonal anti-Ki67 (1:25) (RM-9106-R7; NeoMarker, Fremont, Calif.), rabbit polyclonal anti-p27 (1:1000) (sc-527; Santa Cruz Biotechnology, Santa Cruz, Calif.), rabbit polyclonal anti-HSP90α and β (1:1000) (PA3-012, PA3-013; Affinity Bioreagents, Golden, Colo.). Secondary antibodies coupled to horseradish peroxidase, Alexa-444, Alexa-555, or biotin were obtained from Amersham Pharmacia Biotech (Diegem, Belgium) or Invitrogen. The nuclear stain, 4',6-diamidino-2-phenylindole (DAPI), and a filamentous actin stain, phalloidin-tetramethyl rhodamine isothiocyanate (TRITC), were purchased from Sigma-Aldrich.

The HSP90 inhibitors, geldanamycin (GA) and 17-(allylamino)-17-demethoxygeldanamycin (17-AAG) were purchased from Biomol (Exeter, UK). A rabbit polyclonal anti-HSP90α neutralizing antibody (SPS-771) and the HSP90α and HSP90β recombinant proteins were obtained from Stressgen (Ann Arbor, Mich.). Recombinant proMMP-2 protein and the human Proteome Profiler apoptosis antibody array were obtained from R&D systems (Minneapolis, Minn.). The apoptosis array allows the simultaneous detection of 35 apoptosis and proliferation-related proteins in a single sample and was used according to the manufacturer's protocol.

Invasion Assays

For the type I collagen invasion assay, the following pre-cooled components were gently combined and defined as type I collagen solution: four volumes of type I collagen (stock is 3.49 mg/mL), five volumes of calcium- and magnesium-free Hank's balanced salt solution, one volume of MEM (10×), one volume of 0.25 M NaHCO3, 2.65 volumes of culture medium and 0.3 volumes of 1 M NaOH. For each test-condition, 1.25 mL of type I collagen solution was added to one well of 6-well plate, homogeneously spread and gelified on a flat surface in a humidified atmosphere of 10% CO2 in air at 37° C. for at least one hour. GFP or Rab transfected MCF-7, T47D, or ZR75.1 single-cells ($2 \times 10^5$) suspended in 1 mL culture medium were seeded on top of the type I collagen gel and incubated on a flat surface in a humidified atmosphere of 10% CO2 in air at 37° C. Test products such as GA, 17-AAG, anti-HSP90α neutralizing antibody and HSP90 recombinant proteins were added to the culture medium in the desired concentrations.

Cell morphology was studied and invasion was scored after 24 hours (De Wever et al., (44)). The factor shape refers to a value that is affected by an object's shape but is independent of its dimensions. It was calculated as $(\text{perimeter})^2 \div (4\pi\, \text{area})$, which describes the deviation of an object from a geometric circle. It gives a minimal value of 1 for a perfect circle and larger values for shapes having a higher ratio of perimeter to area. The number of invasive and non-invasive cells was counted in ten randomly selected microscopic fields with a 20× objective and 10× eye piece by two blinded observers using an inverted phase contrast microscope (DMI 3000B, Leica, Wetzlar, Germany). The invasion index was calculated as the ratio of the number of cells that invaded the gel divided by the total number of cells counted in each field. Collagen matrices were fixed in 3% paraformaldehyde for 10 minutes and phalloidin-TRITC stained as previously described (28). Cells were imaged with a Zeiss 510 META confocal laser-scanning microscope (Carl Zeiss, Micro-imaging Inc., Heidelberg, Germany) using a 488 argon and a 543 helium-neon laser. Images were acquired using a Plan Apochromat 63× Phase 1.4 oil differential interference contrast (DIC) objective or a Plan Apochromat 100× Phase 1.4 oil DIC objective. All of the images shown are collapsed z-stacks.

For the Matrigel invasion assays, $10^5$ cells in serum-free culture medium were plated in the top transwell chamber with Matrigel-coated membrane (24-well insert; pore size 8 μm; Becton Dickinson), culture medium was used as a chemoattractant in the lower chamber (27). After 48 hours, a cotton swab removed the cells that did not invade through the pores. Cells on the lower surface of the membrane were stained with DAPI. Invasive cells were counted in 10 microscopic fields per filter using a fluorescence microscope (Axiovert 200M, Carl Zeiss) with a 40× objective (29).

Protein Analysis

For Western blot analysis MCF-7 cells ($1-10\times10^6$) were harvested in Laemmli lysis buffer (0.125 M Tris-HCl [pH=6.8], 10% glycerol, 2.3% SDS). Cell lysates (25 μg) and CM (20 μL) were suspended in 10 μL reducing sample buffer (1M Tris-HCl [pH=6.8], 30% glycerol, 6% SDS, 3% β-mercaptoethanol, 0.005% bromophenol blue) and boiled for 5 minutes at 95° C. Samples were run on NuPage 4-20% Bis-Tris gradient gels (Invitrogen), transferred to PVDF membranes, blocked in 5% non-fat milk in PBS with 0.5% Tween-20, and immunostained. Scanning densitometry was carried out with the Quantity One Program (Bio-Rad).

Quantitative determination of HSP90α in medium that was conditioned by MCF-7 breast cancer cells stably expressing GFP and GFP-Rab27B was performed with a HSP90α ELISA kit (Stressgen) according to the manufacturer's instructions.

For gelatin zymography, CM (20 μL) was resuspended in 10 μL non-reducing sample buffer (0.5 M Tris-HCl [pH=6.8], 20% glycerol, 4% SDS, 0.005% bromophenol blue) without boiling. Samples were loaded on Novex 10% zymogram gelatin substrate gels (Invitrogen). After electrophoresis, gels were washed twice for 30 minutes in a 2% Triton X-100 (Bio-Rad) water solution at room temperature and incubated overnight at 37° C. in MMP substrate buffer (50 mM Tris-HCl [pH 7.5], 10 mM $CaCl_2$). Gels were rinsed again in distilled water and stained with Coomassie Brilliant Blue as described above. Proteolytic activities appeared as clear bands of lysis against a dark background of stained gelatin.

Flow Cytometric Cell Cycle Analysis and Cell Proliferation Assay

For analysis of cell cycle distribution, the Coulter DNA Prep Reagents Kit (Beckman Coulter) was used. Serum-induced cell cycle progression was analyzed by growing MCF-7 GFP and GFP-Rab27B stably transfected cells to 50% confluence, followed by serum starvation for 24 hours, and incubation in Dulbecco's Minimal Essential Medium supplemented with 0.5% fetal bovine serum, 100 U/mL penicillin, and 100 μg/mL streptomycin (Invitrogen) for 24 hours. Cells were harvested by trypsinization, washed with PBS and exposed to DNA Prep Lyse for 1 minute, followed by incubation with DNA Prep Stain for 15 minutes at room temperature in the dark. Cellular DNA content was monitored on a Beckman Coulter Cytomics FC500 flow cytometer (Beckman Coulter). Cell cycle fractions were quantified using WinCycle software (Phoenix Flow Systems).

To examine whether Rab27B affects cell proliferation in a GTP-, geranylgeranyl-, and HSP90α-dependent manner, three sets of experiments were conducted: 1) proliferation rates of MCF-7 cells stably expressing GFP, GFP-Rab27B, GFP-Rab27B Q78L, GFP-Rab27B T23N, and GFP-Rab27B GER were compared; 2) proliferation rates of MCF-7 GFP-Rab27B cells transiently targeted with control or Rab27B siRNAs were studied; and 3) proliferation rates of MCF-7 GFP cells, treated with recombinant HSP90α, and MCF-7 GFP-Rab27B cells, challenged with control IgG or anti-HSP90α neutralizing antibody, were evaluated. To obtain a growth curve under each condition, triplicate wells of seeded cells were each counted five times. Two investigators independently counted the total number of cells in each well every 2 days for a total of 8 days with the use of a manual hemocytometer.

Animal Studies

Animal studies were in accordance with a protocol approved by the Local Ethics Committee of Ghent University Hospital. At the age of 4 weeks (1 week before cell inoculation), female Swiss nu/nu mice (10 mice per group) (Charles River Laboratories, Brussels, Belgium) were primed with a 1 mg estradiol pellet (Organon Laboratories, Cambridge, U.K.) implanted subcutaneously in the neck through surgical incision. Viable cells were injected into the mammary fat pad as a 50 μL suspension of $10^6$ cells in Matrigel (Becton Dickinson). Tumor volume was estimated by using the equation, $V=0.4 \times a \times b^2$, where V is volume, a is the length of the major axis of the tumor, and b is the length of its minor axis. Intraperitoneal metastasis formation was assessed weekly via palpation and visual analysis of the blue and swollen appearance of the abdomen. Mouse survival time was defined as the time from injection until the animals died or were euthanized by cervical dislocation per the protocol approved by the ethics committee, which specifically limited hemorrhagic ascites formation.

Development of ascites was monitored by the measurement of abdominal circumference and body weight. Ascites formation was scored positive when the abdominal circumference increased at least 15%. For the assessment of survival, per Local Ethics Committee of Ghent University Hospital guidelines, mice were euthanized when the abdominal circumference increased 60% above normal controls. Ascites fluid was collected and hematological parameters (number of erythrocytes, hemoglobin and hematocrit) were evaluated by flow cytometry using an ADVIA 120 Hematology System (Bayer Corporation, Tarrytown, N.Y.).

Primary tumors and peritoneal metastasis were extracted, weighed, and fixed in 4% buffered formol for 12 hours, followed by a wash with PBS and transfer to 70% ethanol, and then embedded in paraffin, sectioned, and stained with hematoxylin and eosin (H&E). Lung, liver, and spleen were analyzed for macroscopic metastasis Immunohistochemistry (IHC) using anti-Rab27B and anti-Ki67 antibodies was performed on paraffin sections, using a NexES automated slide staining system (Ventana Medical Systems, Tucson, Ariz.). Primary tumors were scored as invasive if they were firmly attached to the abdominal wall and if H&E staining revealed massive infiltration of the muscular tissue of the abdominal wall by cancer cells. Proliferation was quantified as the percentage of Ki67-positive cancer cells per high power field (objective 40× and eye piece 10×) averaged across 18 images from a total of three primary tumors per cell line.

GFP-Rab27B Vesicle Isolation

Parental or GFP-Rab27B MCF-7 cells ($2 \times 10^8$ cells) were trypsinized and resuspended in culture medium. The cell suspension was centrifuged for 10 minutes at 500×g, followed by three washes with 5 mL Dulbecco's phosphate buffered saline ($PBS^{D+}$). The cell pellet was resuspended in 1 mL homogenization solution (250 mM sucrose in $PBS^{D+}$ supplemented with protease inhibitor cocktail (Roche Applied Science, Indianapolis, Ind.). Cells were homogenized on ice via sonication on a Vibracell VCX130 (4 pulses of 5 seconds with amplitude of 30% each separated by 15 second intervals) (Sonics and Materials Inc., Newton, Conn.). Different centrifugations were performed using a 70.1 Ti rotor Beckman Coulter centrifuge (Beckman Coulter, Fullerton, Calif.): low speed centrifugation at 3,000×g for 10 minutes at 4° C., followed by high speed centrifugation at 30,000×g for 60 minutes at 4° C. A sample of the supernatant and the pellet was collected after each centrifugation step to confirm the presence of vesicle membrane-bound GFP-Rab27B in the supernatant via Western blot analysis. Next, the supernatant was incubated at a 1:1 ratio (v/v) with anti-GFP-labeled magnetic microbeads suspended in homogenization solution (50 μL microbeads/$10 \times 10^6$ cells) (MACS MicroBeads, Miltenyi Biotec, Auburn, Calif.) for 30 minutes on ice. Total samples (2 mL) were loaded on the automated MACS separator (Miltenyi Biotec). Vesicles were eluted in elution buffer (Miltenyi Biotec). After elution, homogenization buffer was added in a 1:1 (v/v) ratio. The purity of the vesicle fraction was checked before and after magnetic separation via flow cytometry (Calibur, Becton Dickinson, Franklin Lakes, N.J.). Vesicles were pelleted by centrifugation at 140,000×g for 1 hour.

Liquid Chromatography-Mass Spectrometry/Mass Spectrometry (LC-MS/MS)

Vesicle pellets and CM (20 μL) were suspended in 60 μL and 10 μL reducing sample buffer respectively (1M Tris-HCl [pH=6.8], 30% glycerol, 6% SDS, 3% β-mercaptoethanol, 0.005% bromophenol blue) and boiled for 5 minutes at 95° C. Samples were run on NuPAGE 4-20% Bis-Tris gradient gels (Invitrogen) in denaturating sodium dodecyl sulphate buffer, stained with 0.5% Coomassie Brilliant Blue (Bio-Rad, Hercules, Calif.) in 40% methanol and 10% acetic acid for 20 minutes, and destained in a solution composed of 40% methanol and 10% acetic acid. Gel bands were processed and analyzed by LC-MS/MS as previously described (25). Raw MS/MS files were submitted to the NIH MASCOT Cluster (26) using MASCOT DAEMON. Data were searched against the UNIPROT-SPROT+UNIPROT-TREMBL database as described (25). For each peptide identification, MASCOT reports a probability-based ion score, which is defined as $-10 \cdot \log 10(P)$, where P is the absolute probability that the observed match between the experimental data and the database sequence is a random event. The significance threshold for inclusion of each peptide in the output file is the individual ion score meeting or exceeding its MASCOT identity score threshold ($P<0.05$). MASS SIEVE was used to parse the MS/MS data from MASCOT and generate protein parsimony reports worldwideweb at proteomecommons.org/dev/masssieve). Each protein was assigned to the functional classification based on the Gene Ontology annotation system using the DAVID database bioinformatics resources worldwideweb at david.abcc.ncifcrf.gov). Only peptides that were detected in two separate experiments were retained.

Patient Samples, Quantitative RT-PCR, Immunohistochemistry and FISH

Clinical data and primary breast carcinoma samples were collected for every consecutive patient with stage I to IV breast cancer at Ghent University Hospital between Jan. 11, 2008 and Dec. 31, 2008. Written informed consent was obtained from each patient according to the recommendations of the local ethics committee. Adjacent histologically normal breast tissue was collected in the same tissue sample from each patient. One part of the tumor, with adjacent normal tissue, was snap-frozen immediately and stored at −80° C. for blinded quantitative RT-PCR and Western blot analysis and one part containing tumor and normal cells was formalin-fixed for Rab27B IHC.

Western blotting was performed on lysates prepared from microdissected tumor tissue. Briefly, one H&E stained section was mounted with a cover slip, and the remaining adjacent serial sections were left without a cover slip for tissue removal. Using the covered H&E-stained slide as the template, areas that were not of interest (containing stroma and accumulated collagen) were removed. The remaining epithelial tissue, obtained from a minimum of 10 sections, was lysed and analyzed by Western blotting.

The Rab27B protein IHC signal was scored on the following scale taking into account both the proportion of cells stained and the intensity staining in those cells: score 0, weak or absent cytoplasmic staining and fewer than 5% of cancer cells containing Rab27B localized to the plasma membrane or vesicle clusters; score 1, cytoplasmic staining and between 5 and 30% of the cancer cells containing Rab27B localized prominently to the plasma membrane or clustered vesicles; score 2, cytoplasmic staining and more than 30% of the cancer cells containing Rab27B localized prominently to the membrane and vesicles; two observers quantified independently.

Total RNA was isolated using the Trizol reagent (Invitrogen) according to the manufacturer's protocol. RNA was treated with a DNase kit (DNA-free) to remove all remaining DNA according to the manufacturer's protocol (Applied Biosystems, Austin, Tex.). RNA concentration and purity were measured on the Nanodrop ND-1000 (Nanodrop Technologies, Wilmington, Del.). First strand cDNA was synthesized using a high capacity RNA-to-cDNA kit (Applied Biosystems) according to the manufacturer's guidelines. Q-RT-PCR was performed utilizing 100 ng cDNA, Taqman gene expression master mix reagent and Assays-On-Demand (Applied Biosystems) for Rab27B (Assay ID Hs00188156_m1), Rab27A (Assay ID Hs00608302_m1), Rab3D (Assay ID Hs00269915), and a control gene, PIAA (37), (Assay ID Hs99999904_m1) on an ABI PRISM 7900 HT Sequence Detection System (Applied Biosystems) using the comparative $C_T$ method ($\Delta\Delta C_T$); an approach to measure relative gene expression. The cycling conditions were as follows: 2 minutes at 50° C., 10 minutes at 95° C., and 40 cycles at 95° C. for 15 seconds and 60° C. for 60 seconds (30).

Fluorescence in situ hybridization (FISH) was performed with a dedicated Rab27B probe set (RP11-99A1 and RP11-839G9; Chori, BACPAC Resources, Oakland, Calif.). Deparaffinized and heat-pretreated tissue sections were digested with pepsin (8.5 mM NaCl [pH=2]; Sigma) and dehydrated in graded ethanol (75%, 80%, and 100%). The tissues on the slides were denatured at 82° C. for 5 minutes and hybridized at 45° C. for 18 hours with the Rab27B probe set in a S2450 Hybridizer Instrument for In Situ Hybridization (DAKO, Stockholm, Sweden). In each case, 20 non-overlapping, intact, interphase tumor nuclei identified by DAPI staining were evaluated, and Rab27B copy numbers in each nucleus were assessed. The patient samples were considered to contain amplified, or polysomic Rab27B gene expression if more than two signals were seen in at least 10% of the tumor cells.

Statistical Analysis

All statistical calculations were performed using MedCalc (Version 11.0, Mariakerke, Belgium). Comparisons were performed using a two-sided unpaired Student's t-test following D'Agostino-Pearson testing for normal distribution (Matrigel invasion assays, factor shape calculation, Ki67 proliferation index and tumor weight) or $\chi^2$-test (collagen type I invasion assays). For the cell proliferation assays data were compared by two-way repeated measures analysis of variance (ANOVA) test. Kaplan-Meier curves and log-rank testing were used for survival analyses. Rab27B, Rab27A and Rab3D mRNA levels in clinical samples were compared with the Mann-Whitney rank sum test. Frequency tables of the Rab27B immunohistochemistry data were analyzed by the $\chi^2$-test. All data presented are representative of at least three independent experiments. All statistical tests were two-sided. P-values less than 0.05 were considered to be statistically significant, and where appropriate the difference of means and the 95% confidence interval (95% CI) are indicated.

Results

Effect of Rab27B Overexpression on Morphology and Invasion

Figure 1:
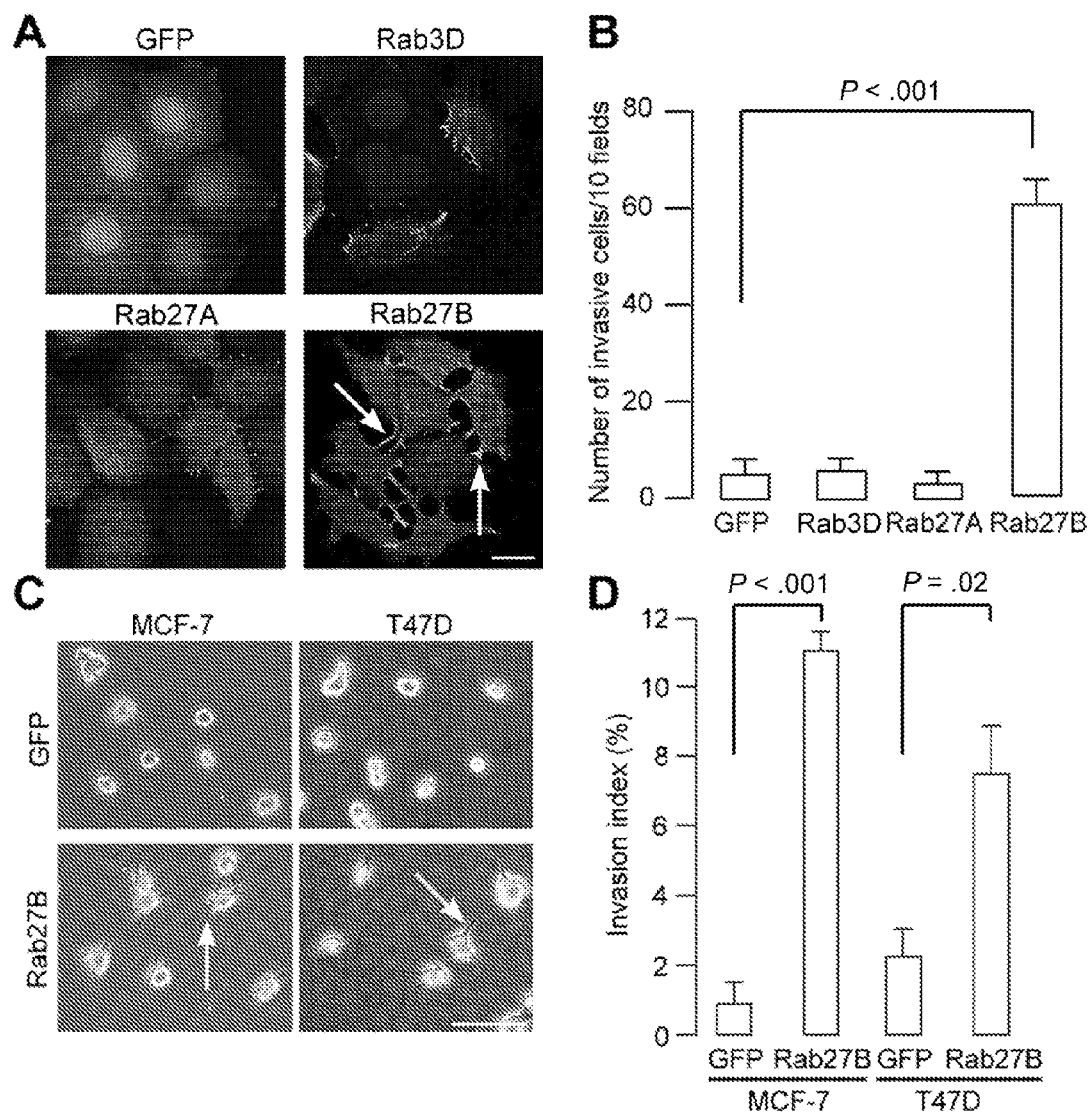
FIG. 1. Effect of ectopic expression of Rab3D, Rab27A, or Rab27B on the formation of cellular extensions and invasiveness. A) Morphology of MCF-7 cells transiently transfected with GFP, GFP-Rab3D, GFP-Rab27A or GFP-Rab27B expressing plasmids. 24 hours after transfection, cells were fixed and nuclei were stained with DAPI. Laser scanning confocal images show punctuate GFP signal that is indicative of localization of GFP-fusion protein to vesicles. Scale bar, 20 μm. B) Matrigel invasion assay with GFP-Rab transfected MCF-7 cells. 24 hours after transient transfection with GFP-Rab expressing plasmids, $10^5$ MCF-7 cells were seeded on top of a Matrigel-coated filter and their migration towards medium containing serum was quantified by microscopic evaluation (total magnification 400×). The mean total number of invading cells counted after 72 hours from 10 different fields is shown with the upper 95% confidence intervals from the means of three independent experiments performed in triplicate. P-values were calculated using two-sided Student's t-tests. Statistically significant P-values are indicated. C and D) Morphology and invasiveness of GFP-Rab transfected MCF-7 and T47D breast cancer cells. In (C) phase contrast images are shown of cells seeded on type I collagen matrix 24 hours after transient transfection. In (D) the invasion index was calculated by counting the number of invading and non-invading cells into type I collagen matrix in ten fields. Invasion indices are means and upper 95% confidence intervals derived from the means of three independent experiments performed in triplicate. P-values were calculated using $\chi^2$-tests; statistically significant P-values are indicated. Scale bar, 50 µm. In (A) and (C), arrows indicate cellular extensions and local spreading.

After transient transfection of human MCF-7 breast cancer cells, GFP-tagged Rab3D, Rab27A, and Rab27B each displayed a vesicular distribution (FIG. 1,A). MCF-7 cells transfected with a GFP control plasmid exhibited no morphological changes, whereas those transfected with GFP-Rab3D or GFP-Rab27A exhibited limited ruffling at the cell surface (FIG. 1,A). By contrast, cells in which GFP-Rab27B was overexpressed formed cellular extensions and a spread morphology, and had a statistically significantly increased ability to invade Matrigel compared with the other three transfected cell types (number of invading cells, Rab27B-expressing vs control, mean=60.1 vs 5.0 cells, difference=55.1 cells, 95% CI=49.6 to 60.6 cells; P<0.001) (FIG. 1,B). When MCF-7, T47D, or ZR75.1 breast cancer cells were transfected with GFP-Rab27B, the cells assumed a similarly changed morphology and were more invasive than control cells on a type I collagen substrate (number of invading cells of the total number of cells, Rab27B-expressing vs control: MCF-7 cells, 24 of 234 [10%] vs 2 of 212 [0.9%], P<0.001); T47D cells, 16 of 229 [7%] vs 5 of 215 [2%], (P=0.02). GFP-Rab27A and GFP-Rab3D had no such effect (FIGS. 1, C and D).

Involvement of Rab27B in Matrix Invasion and G1 to S Phase Cell Cycle Progression Next, we established MCF-7 cells that stably expressed GFP, GFP-Rab27B, GFP-Rab27A, and each of four mutants of GFP-Rab27B; GFP-Rab27B Q78L is a constitutively active mutant defective in GTP hydrolysis, GFP-Rab27B-T23N and GFP-Rab27B-N133I are dominant negative mutants defective in GTP binding, and the GFP-Rab27B-GER mutant is impaired in geranylgeranyl modification and vesicle membrane targeting.

Figure 2:
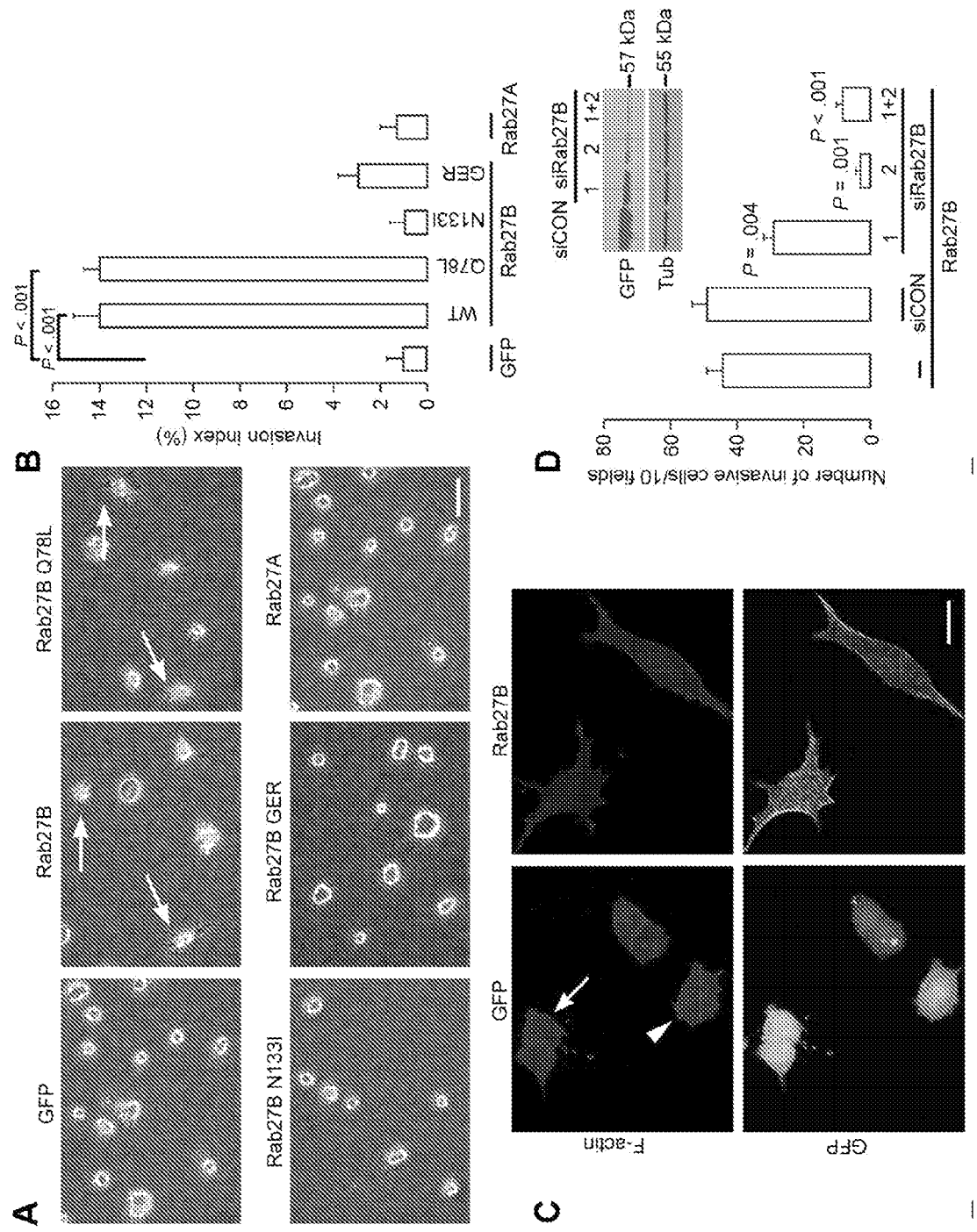
FIG. 2. Rab27B GTP- and geranylgeranyl-dependent cancer cell invasion and cell cycle progression in vitro. A) Phase contrast images showing morphology of MCF-7 cells stably transfected to express GFP, GFP-Rab27A, GFP-Rab27B (wild type, WT), or GFP-Rab27B mutants. GFP-Rab27B Q78L (constitutive active), N133I (dominant negative) and GER (impaired geranylgeranylation and vesicle targeting) were the mutants used. Arrows indicate cellular extensions and local spreading. Scale bar, 50 µm. B) Quantification of type I collagen invasion by the cells shown in (A). Invasion assays were performed as in FIG. 1,D. Invasion indices are means and upper 95% confidence intervals derived from the means of three independent experiments performed in triplicate. P-values were calculated using $\chi^2$-tests. Statistically significant P-values are indicated. C) Laser scanning confocal images of the F-actin cytoskeleton (phalloidin-TRITC) and GFP localization in MCF-7 GFP and GFP-Rab27B cells cultured for 24 hours on a collagen type I matrix. Arrow indicates cortical F-actin and arrowhead indicates membrane blebs. Scale bar, 20 µm. D) Invasion by Rab27B-expressing MCF-7 cells in which Rab27B was depleted. MCF-7 cells that expressed GFP-Rab27B, with or without transfection of control siRNA (siCON) or Rab27B siRNAs (siRab27B 1 and/or 2), were seeded on a Matrigel-coated filter. The inset panel shows the impact of the Rab27B siRNAs on Rab27B expression in these cells by immunoblotting. The numbers of invasive cells were counted after 72 hours in 10 different fields and are expressed as the mean with upper 95% confidence intervals of three independent experiments performed in triplicate. P-values shown are for comparisons with the siCON transfection using two-sided Student's t-tests. E) Effect of Rab27B on cell cycle progression. MCF-7 GFP and GFP-Rab27B cells were grown to 50% confluence, followed by 24 hours serum starvation, and 24 hours serum-induced (0.5%) cell cycle progression. Percentages of MCF-7 GFP and GFP-Rab27B cells in G1, S and G2 stage of the cell cycle, as measured by flow cytometry, are represented as the means with upper 95% confidence intervals of two independent experiments. F) Western blot analysis in mutant Rab27B-transfected MCF-7 cells of the positive (cyclin A and E) and negative (p27) G1 to S phase cell cycle regulators. Protein levels were quantified as immunostaining intensity relative to tubulin. G) Measurement of cell proliferation rates of MCF-7 cells stably expressing GFP, GFP-Rab27B, or GFP-Rab27B mutants as in (A). 10 000 cells were plated into each well of a total of 15 wells on day 1 in order to establish one growth curve under each condition in triplicate. The total number of cells per well was manually counted every 2 days until day 8. Mean number of cells is plotted with upper 95% confidence intervals. P-values were calculated using the two-way repeated measures ANOVA test. Statistically significant P-values are indicated; data were compared with the GFP control. H) Measurement of cell proliferation rates of MCF-7 GFP-Rab27B cells transiently transfected with control (siCON) or pooled Rab27B siRNAs (siRab27B1 and 2). The experiment was performed as in (G). An inset panel shows the effect of this siRNA on cyclin A expression in MCF-7 GFP-Rab27B cells. Tubulin was used as loading control.
Figure 2:
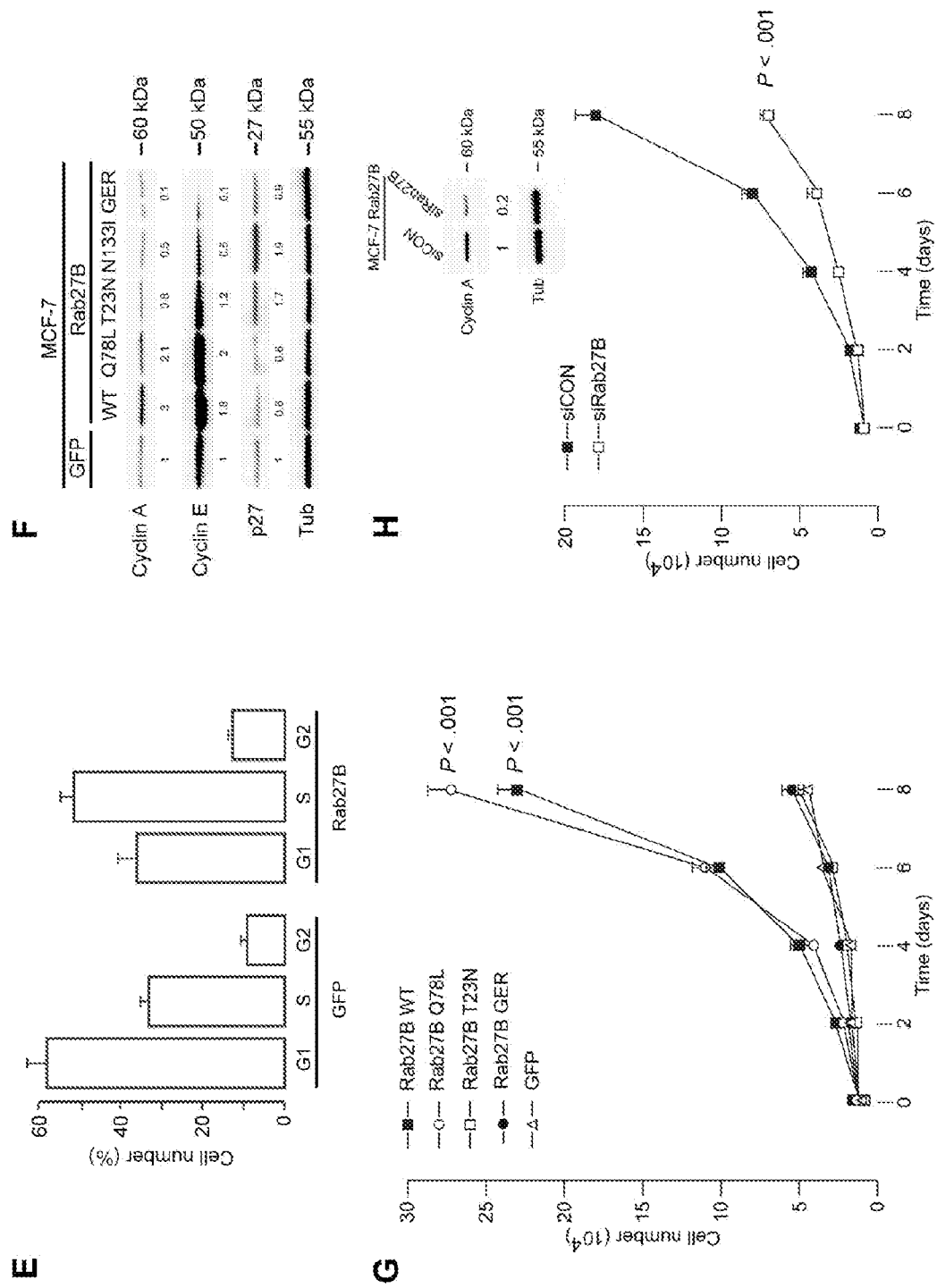

Laser scanning confocal microscopy revealed a vesicular distribution for the GFP-Rab27A, GFP-Rab27B and GFP-Rab27B-Q78L proteins in these cells, but a complete loss of vesicular localization for the GFP-Rab27B-T23N and GFP-Rab27B-GER proteins. Local spreading and invasion in type I collagen, apparent in GFP-Rab27B transfected breast cancer cells, were also characteristic of GFP-Rab27B-Q78L-transfected cells (number of invading cells of the total number of cells, wild type GFP-Rab27B-expressing cells vs GFP-Rab27B-Q78L-expressing cells vs control: 27 of 224 [12%] vs 27 of 210 [13%] vs 3 of 211 [1%]; (P<0.001, for both GFP-Rab27B WT and Q78L vs control) (FIGS. 2, A and B). By contrast, GFP-Rab27A, GFP-Rab27B-T23N, GFP-Rab27B-N133I, and GFP-Rab27B-GER-expressing MCF-7 cells did not change morphology nor invade the collagen matrix. F-actin staining with phalloidin-TRITC revealed a rounded appearance for MCF-7 GFP control cells, with membrane blebs and prominent cortical F-actin (FIG. 2,C). MCF-7 GFP-Rab27B cells showed elongated cell morphology, with multiple protrusions. GFP-Rab27B vesicles accumulated at the cell periphery (FIG. 2,C). We quantified cell spreading by calculating the factor shape of the cells, (perimeter)$^2 \div (4\pi$ area), which describes the deviation of the shape from a geometric circle. For control cells, this value was 1.65±0.23, indicating poor spreading; for GFP-Rab27B cells, the value was 5.59±0.35, indicating statistically significant spreading (difference=3.94, 95% CI=3.74 to 4.13; P<0.001). Transient targeting of Rab27B by single or pooled siRNAs depleted Rab27B protein by 70-80%, as assessed by western blotting, and was accompanied by loss of the elongated cell morphology (factor shape value, after transfection with pooled siRNAs, was 2.1±0.3) and loss of invasion into Matrigel and collagen type I matrices (FIG. 2,D).

Next, we investigated the impact of Rab27B expression on cell cycle progression and proliferation. The results of a screen using a commercial "proteome profiler" antibody array indicated that ectopic expression of GFP-Rab27B was associated with a mitogenic signature in MCF-7 cells (data not shown). Cell cycle progression was studied by flow cytometric cell cycle analysis after serum starvation followed by readdition of 0.5% serum. We found that GFP-Rab27B initiates G1 to S phase transitions in MCF-7 cells (FIG. 2, E). In addition, expression of the positive cell cycle regulators cyclin A and cyclin E increased, whereas expression of the negative cell cycle regulator p27 decreased, in MCF-7 cells transfected with GFP-Rab27B or GFP-Rab27B-Q78L (FIG. 2, F). By contrast, transfection of GFP-Rab27B-T23N, -N133I, or -GER was associated with increased expression of p27 but reduced expression of cyclin A and cyclin E. MCF-7 cells that expressed GFP-Rab27B consistently demonstrated much higher levels of cell proliferation than control cells transfected with only GFP at limiting (0.5%) serum concentrations (P<0.001) (FIG. 2, G). Furthermore, GFP-Rab27B enhanced MCF-7 proliferation under limiting serum concentrations in a GTP- and geranylgeranyl-dependent manner. A similar enhancement of growth under low serum concentrations was observed following transfection of GFP-Rab27B into T47D and ZR75.1 breast cancer cells (data not shown). In supporting experiments, transient targeting of Rab27B by a combination of both siRNAs precluded Rab27B-stimulated proliferation (P<0.001) and Rab27B-induced cyclin A expression (FIG. 2, H).

Effect of Rab27B Overexpression on Invasive Tumor Growth in Nude Mice

Figure 3:
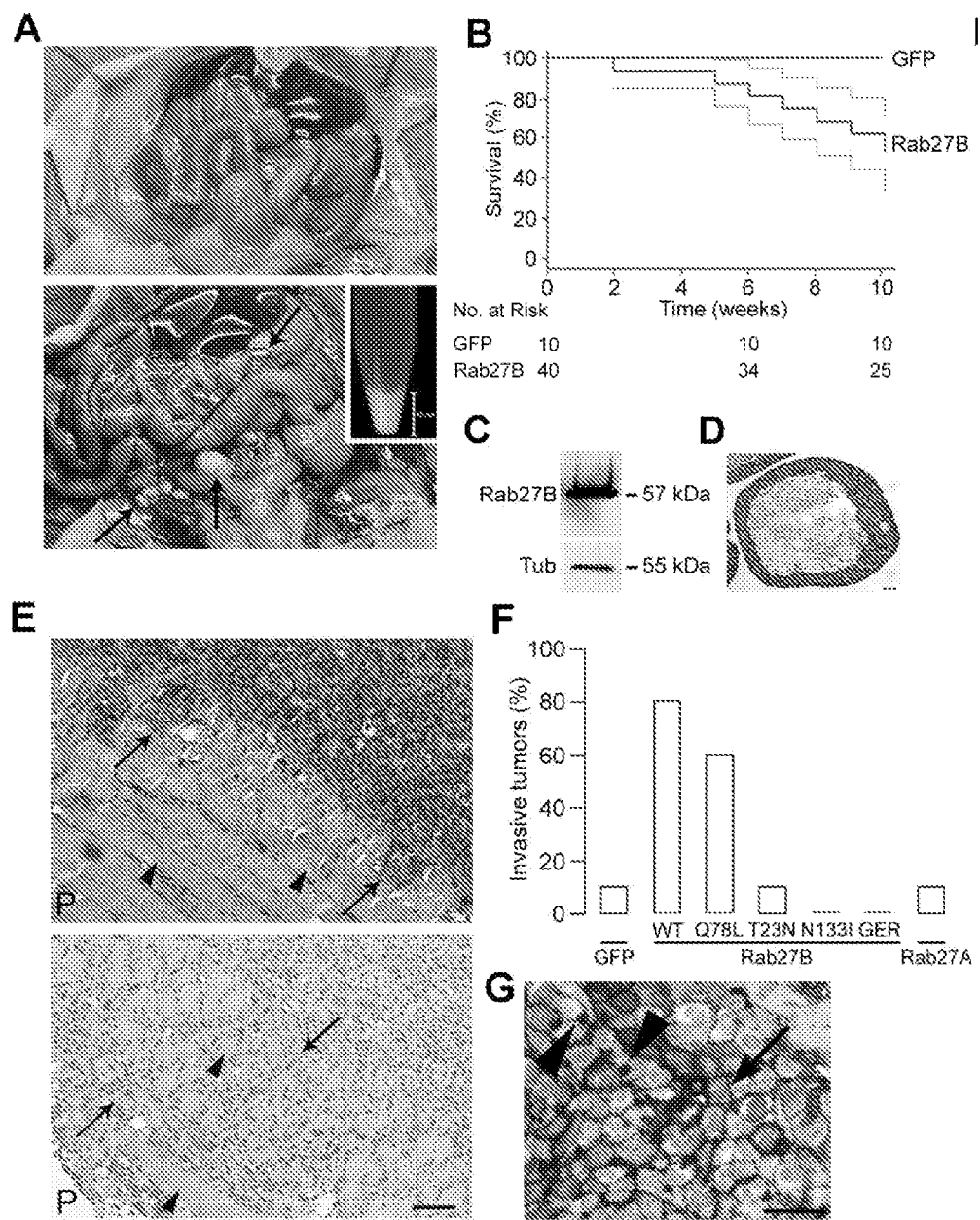
FIG. 3. Effect of Rab27B on invasive tumor growth in vivo. Nude mice were injected in the mammary fat pad with MCF-7 cells expressing GFP, GFP-Rab27A, GFP-Rab27B (wild type, WT), or mutant GFP-Rab27B proteins (Q78L, T23N, N133I, and GER). A) Tumorigenesis in nude mice with MCF-7 GFP-Rab27B xenografts vs controls. Mice with MCF-7 GFP-Rab27B xenografts (lower panel) developed hemorrhagic ascites (blue and swollen appearance of the ventral side) and tumor aggregates (arrow) in the peritoneal cavity and attached to organs such as the ovary. MCF-7 GFP xenografts (upper panel) developed no hemorrhagic ascites. Inset: Pelleted tumor aggregates from the peritoneal fluid of one mouse. Scale bar, 13 mm. B) Effect of Rab27B expression on survival of mice with xenografts. Kaplan-Meier curves and log-rank testing (95% confidence intervals, P=0.031) are shown for nude mice injected with MCF-7 GFP cells (n=10) versus MCF-7 GFP-Rab27B cells (n=40; four different clones with 10 mice per group). C) Expression of GFP-Rab27B in tumor aggregates. A western blot loaded with 60 µg peritoneal tumor aggregate and immunostained with primary Rab27B and tubulin antibodies is shown. D) Hematoxylin and eosin (H&E) staining of a peritoneal tumor aggregate. Scale bar, 100 µm. E) H&E staining of MCF-7 GFP (upper panel) and GFP-Rab27B (lower panel) xenografts. Arrowheads indicate striated muscle tissue; arrows indicate areas of muscular invasion by cancer cells to the peritoneal side (P). Scale bar, 100 µm. F) Relative invasiveness of xenografts expressing WT and mutant Rab27B proteins. Percentage of invasive tumors was determined by the total number of mice with an invasive xenograft in the peritoneal wall as assessed by macroscopic observation and immunohistochemistry (n=10 mice per group). Precise percentages for a single experiment are shown. G) Cellular localization of Rab27B in MCF-7 GFP-Rab27B xenografts. Arrow indicates peripheral Rab27B distribution; arrowheads indicate Rab27B vesicle clustering appearing in the cytoplasm and at cell-cell contact. Scale bar, 25 µm. H) Mean tumor volume in nude mice bearing xenografts that expressed WT or mutant Rab27B proteins (n=10 mice per group). Tumor size was assessed weekly by measurement of the external diameter of the xenografts for 10 weeks. GFP expression was maintained in the xenografts throughout this time period (data not shown). Error bars represent 95% confidence intervals. I) Mean tumor weight after surgical resection of xenografts expressing WT or mutant Rab27B proteins. Mice were killed at variable time points (ie, the ethical endpoint which limits hemorrhagic ascites formation, or the experimental end point at 10 weeks) after injection of stably transfected MCF-7 cells (n=10 mice per group). Error bars represent upper 95% confidence intervals. P-values were calculated using two-sided Student's t-tests; statistically significant P-values are indicated. J) Immunohistochemical staining of MCF-7 GFP and GFP-Rab27B xenografts to detect Ki67, a proliferation marker. The mean number of proliferating MCF-7 GFP-Rab27B cells, calculated from 18 images of three primary tumors per cell line, was 85.50±4.04 vs 32.56±2.68 proliferating control cells (two-sided Student's t-test, P<0.001). Scale bar, 50 µm.
Figure 3:
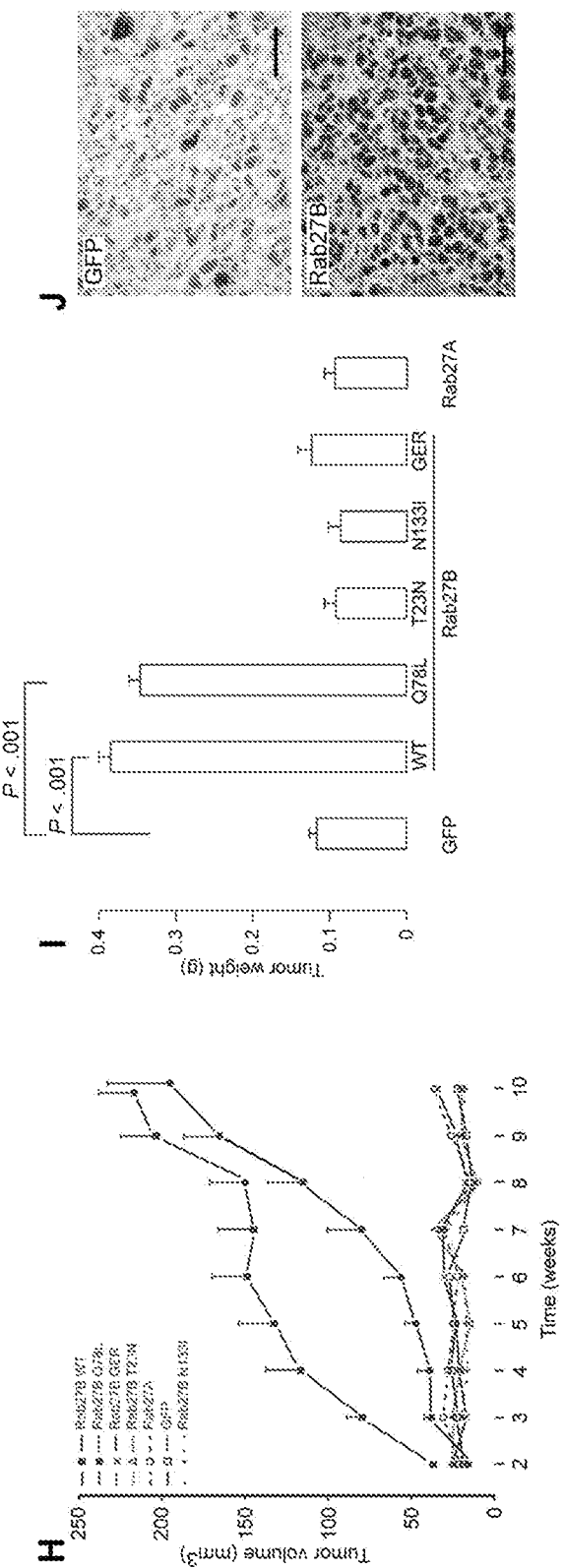

To further investigate whether Rab27B enhances invasive tumor growth in vivo, we implanted $10^6$ MCF-7 cells stably transfected with GFP-Rab27A, or GFP-Rab27B and its mutants, or a similar number of control GFP-transfected MCF-7 cells into the mammary fat pads of Swiss nu/nu mice, and monitored tumor and metastasis formation for 10 weeks. All mice displayed visible mammary tumors 2 weeks after injection. No apparent toxicity was observed in mice bearing control MCF-7 GFP xenografts (n=10), but 37.5% of the mice bearing MCF-7 GFP-Rab27B xenografts (n=40) developed hemorrhagic ascites in the peritoneal cavity that resulted in death (at 10 weeks, MCF-7 GFP vs GFP-Rab27B injected mice, survival was 100% vs 62.5%, hazard ratio of death=0.26, 95% CI=0.08 to 0.88; P=0.03) (FIGS. 3, A and B). Ascites fluid was collected from six of these mice; the mean volume was 1.6±0.2 mL and the number of red blood cells present was approximately 20% of that in the peripheral blood ($2.2\pm0.35\times10^6$/mm$^3$) The tumor aggregates present in the ascites yielded a 57 kDa GFP-Rab27B immunoreactive protein (FIG. 3, C), indicating they were derived from the xenograft, and consisted of a rim of five to ten cell layers surrounding a necrotic center (FIG. 3, D).

The primary MCF-7 GFP-Rab27B xenografts showed massive muscular invasion compared with the MCF-7 GFP xenografts (FIG. 3, E). At 10 weeks, approximately 80% and 60% of nude mice injected with GFP-Rab27B and GFP-Rab27B-Q78L MCF-7 cells, respectively, developed invasive xenografts (FIG. 3, F). By contrast, MCF-7 xenografts that expressed either GFP alone, GFP-Rab27B-T23N, GFP-Rab27B-N133I, GFP-Rab27B-GER or GFP-Rab27A were nearly all noninvasive, ie, confined within fibrotic capsules. Immunohistochemistry of the primary GFP-Rab27B xenograft with a specific Rab27B antibody revealed Rab27B localization in the cytoplasm and at cell-cell contacts (FIG. 3, G). Also at 10 weeks, the MCF-7 GFP-Rab27B and GFP-Rab27B-Q78L xenografts had an approximately eightfold larger volume and fourfold increased resected tumor weight than the MCF-7 GFP, GFP-Rab27B-T23N, GFP-Rab27B-N133I, GFP-Rab27B-GER and GFP-Rab27A xenografts (means: weight of control GFP xenograft=0.11 g, WT xenograft=0.39 g, Q78L xenograft=0.35 g; difference: control vs WT=0.28 g, 95% CI=0.26 to 0.30, P<0.001; difference, control vs Q78L=0.24 g, 95% CI=0.21 to 0.26, P<0.001) (FIGS. 3, H and I). Furthermore, Ki67 staining showed that 86% of MCF-7 GFP-Rab27B cancer cells were in a proliferative state compared with 33% of MCF-7 GFP cells (difference=53%, 95% CI=48% to 58%, P<0.001) (FIG. 3, J).

Functional Implication of HSP90α Secretion in Rab27B-Overexpressing Cells

Figure 4:
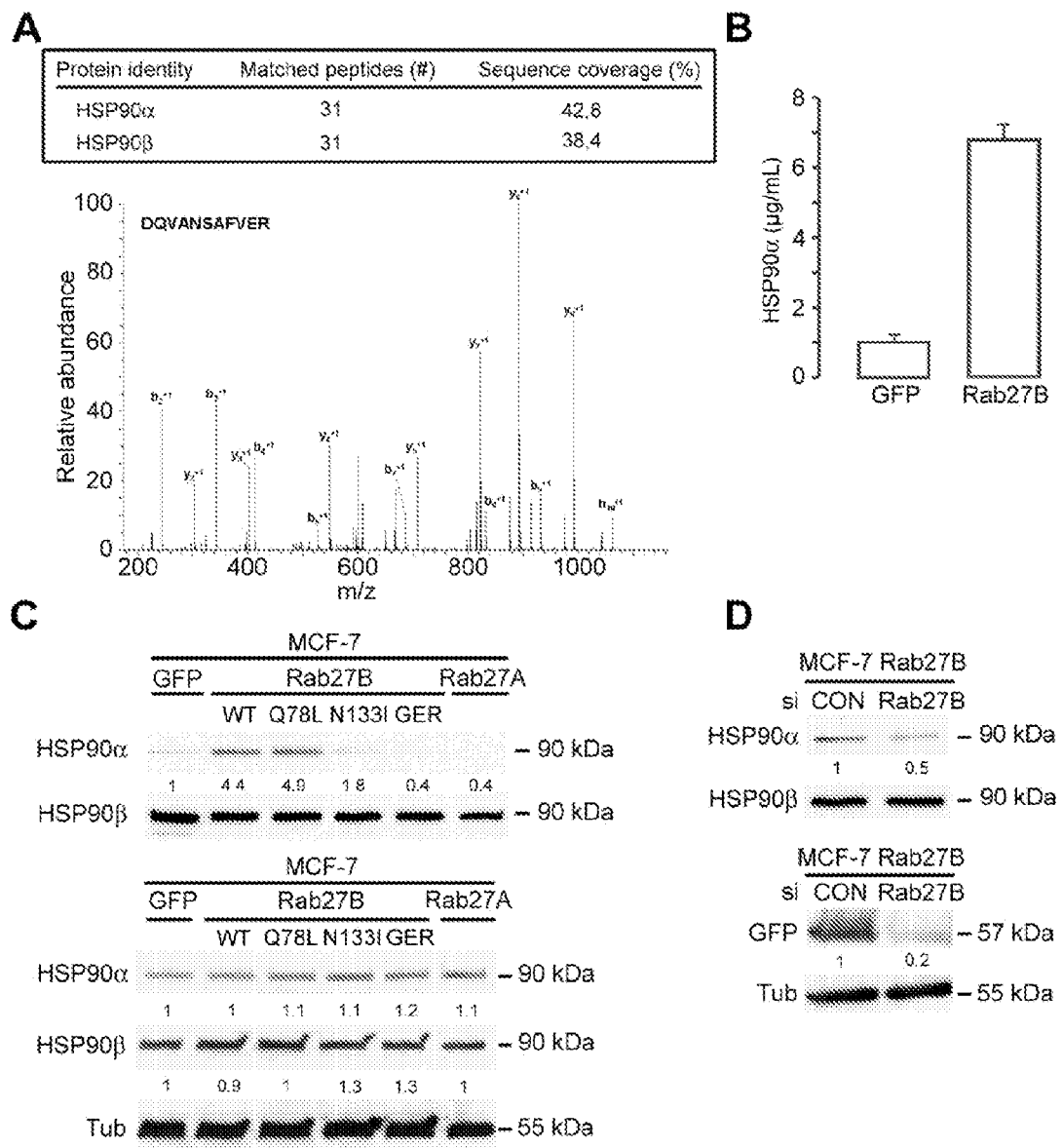
FIG. 4. Selective stimulation of HSP90α secretion by Rab27B through GTP- and geranylgeranyl-dependent mechanisms. A) Secretome profiling of invasive MCF-7 GFP-Rab27B cancer cells identified HSP90α and HSP90β. The number of matched peptides and the percentage of sequence coverage are indicated for both proteins. The MS/MS spectrum recorded on a $[M+2H]^{2+}$ ion at m/z 618.69, corresponds to a unique peptide [DQVANSAFVER (SEQ ID NO:7)], derived from HSP90α. Peptides fragment along the amide backbone to produce sequence-specific fragment ions.

GFP-Rab27B secretory vesicles were isolated from MCF-7 GFP-Rab27B cells by a combination of differential centrifugation and enrichment using anti-GFP antibody-coated magnetic beads and a benchtop automated magnetic cell sorter. Proteomic analysis was performed on 97% pure GFP-Rab27B vesicles, as measured by flow cytometry. HSP90α is known to play an essential extracellular role in cancer cell invasion (31) and was identified with high confidence (ie, in two separate experiments). Polyacrylamide gel analysis of the conditioned media from MCF-7 GFP-Rab27B cells revealed 90 kDa proteins that were identified by mass spectrometry as HSP90α and HSP90β (FIG. 4, A). ELISA assays confirmed that HSP90α secretion was sevenfold higher in the media prepared from MCF-7 GFP-Rab27B cells compared with MCF-7 GFP cells (FIG. 4, B). Western blotting measured HSP90α levels that were 4.4- and 4.9-fold higher in the conditioned media of MCF-7 cells that expressed GFP-Rab27B and constitutively active GFP-Rab27B-Q78L, respectively, compared with media from control MCF-7 GFP cells (FIG. 4, C, upper panel); cells that expressed GFP-Rab27A, GFP-Rab27B-GER, or the GTP-binding mutant showed much less HSP90α secretion, ie, 0.4-fold, 0.4-fold, or 1.8-fold, respectively, that of MCF-7 GFP cells. However, western blot analysis revealed no difference in intracellular levels of HSP90α or β among MCF-7 cells expressing GFP, GFP-Rab27A, and GFP-Rab27B or its mutants (FIG. 4, C, lower panel). In spite of this finding, 60% depletion of Rab27B protein expression by RNA interference (FIG. 4, D, lower panel), was associated with a 50% reduction in HSP90α secretion into the media of GFP-Rab27B MCF-7 cells (FIG. 4, D, upper panel), whereas HSP90β secretion remained unchanged.

In additional experiments, we examined the ability of HSP90 or its inhibitors to affect invasive growth. We first explored the ability of 1 μM concentrations of an HSP90 inhibitor, geldanamycin (GA), or its derivative, 17-AAG (32), to reverse the invasive potential of MCF-7 GFP-Rab27B cells in the type I collagen invasion assay described previously. Each of these drugs was able to inhibit invasion by 85%-100% (P<0.001) (FIG. 5, A) at this concentration, and less than 1% toxicity was observed in Trypan blue exclusion assays. GA and 17-AAG are able to inhibit both secreted and intracellular HSP90α and HSP90β. Therefore, to determine whether invasion could be inhibited by reducing only extracellular HSP90 activity, we also tested the effect of an anti-HSP90α-specific neutralizing antibody, which reversed the invasive phenotype of MCF-7 GFP-Rab27B cells by 4.3-fold (P<0.001) (FIG. 5, B). Finally, we examined whether addition of HSP90 to the cell culture medium could promote invasion. We observed a dose-dependent increase in type I collagen invasion by MCF-7 cells treated with 1-10 μg/mL recombinant HSP90α (P=0.04 at 5 μg/mL, and P=0.003 at 10 μg/mL, $\chi^2$-test) (FIG. 5, C); however, addition of 10 μg/mL recombinant HSP90β had no effect.

Next, we examined the role of HSP90α in Rab27B-induced proliferation and Rab27B-increased cyclin A expression. The anti-HSP90α-specific neutralizing antibody (5 μg/mL) reversed the increased proliferation of MCF-7 GFP-Rab27B cells by fivefold (P<0.001) (FIG. 5, D) and inhibited cyclin A expression by twofold (FIG. 5, E). In accordance, we observed increased proliferation of MCF-7 cells upon addition of 10 μg/mL recombinant HSP90α to the culture medium (P<0.001) (FIG. 5, D) and increased cyclin A expression (FIG. 5, E) at a 10 μg/mL concentration that was similar to that found in the secretome of Rab27B overexpressing cells.

What is the molecular mechanism of HSP90α in promoting invasive growth? It is known that HSP90α serves as an extracellular chaperone for MMP-2, a protease that degrades extracellular matrix (31); the active form is 68 kDa, produced by cleavage of a peptide from the 72 kDa pro-protein. Extracellular 68 kDa MMP-2 activity increased 2.1-fold in MCF-7 cells transfected with GFP-Rab27B and 5.3-fold in MCF-7 cells expressing constitutively active GFP-Rab27B Q78L, but was decreased in MCF-7 variants transfected with the dominant negative or geranylgeranyl mutants of Rab27B (FIG. 5, F). In agreement, recombinant proMMP-2 that was exogenously added to MCF-7 GFP-Rab27B cells was activated in an HSP90α dependent manner as demonstrated by the inhibitory effects of the specific anti-HSP90α-neutralizing antibody (FIG. 5, G).

Expression of Rab27B in Primary Human Breast Tumors

We next analyzed the expression of the Rab27B protein in 59 primary breast tumors by immunohistochemistry using our Rab27B-specific antibody (FIGS. 6, A and B and Table 1). Breast tumors with no or weak cytoplasmic Rab27B expression and with less than 5% of cancer cells showing membrane localization and/or vesicle clustering, ie score=0, were ER-negative (10 of 10, 100%), whereas tumors with cytoplasmic Rab27B distribution and prominent membrane localization and/or vesicle clustering, ie a score 1 or 2, were ER-positive (49 of 49, 100%; P<0.001). Conversely, ER status was perfectly associated with Rab27B status. Furthermore, there was a statistically significant association between Rab27B score 2 (>30% of cancer cells showing prominent Rab27B localization at the plasma membrane or vesicle clusters) and positive lymph node metastases (P<0.001) as well as tumor grade (P=0.001) (FIG. 6, B). Lysates from MCF-7 GFP-Rab27B cells or from epithelial tissues microdissected from fresh frozen primary human breast cancer tissue with immunohistochemical scores of 0, 1 or 2 were subjected to western blotting with our Rab27B-specific polyclonal antibody. Similar Rab27B expression levels were observed in MCF-7 cells that stably expressed ectopic GFP-Rab27B and in microdissected breast tissue with an immunohistochemistry score of 2 (that tended to metastasize more frequently to the lymph nodes). Endogenous Rab27B levels in non-invasive MCF-7 cells had expression levels similar to those in microdissected breast tissue with an immunohistochemistry score of 1 (that had a less aggressive character); ER-negative breast tumors did not express Rab27B.

We next investigated the relative expression of Rab3D, Rab27A, and Rab27B mRNAs in 20 tumor samples by quantitative RT-PCR. Median expression of Rab3D and Rab27A did not statistically significantly differ between normal and tumor tissue (P=1.0 and P=0.369 respectively) (FIG. 6, C). By contrast, median expression of Rab27B was tenfold higher in tumor tissue compared with normal tissue (P=0.004, Mann-Whitney test). To investigate the relationship between Rab27B mRNA expression and clinical parameters, the 20 tumor samples were divided into two groups according to ER status (FIG. 6, D). As might be predicted from our previous immunohistochemistry results, Rab27B mRNA expression levels statistically significantly differed between ER-negative vs ER-positive tumor samples (P=0.019 and P<0.001) whereas no statistically significant difference was observed between normal samples and ER-negative tumors (P=0.22). In addition, the median accumulation of Rab27B mRNA was twofold higher in the ER-positive group of patients with lymph node metastases compared with those without lymph node metastases (P=0.049) (FIG. 6, D). On of the 20 tumor samples we performed both quantitative RT-PCR and immunohistochemistry, and demonstrated that in 14 of 17 (82%) samples analyzed, Rab27B mRNA expression strictly followed protein expression. We performed FISH analysis on 10 tumor samples randomly selected among the 17 tumor samples that had an immunohistochemical score of 2, but this test revealed no amplification of the RAB27B gene (Table 1).

TABLE 1

Tumor composition and Rab27B association with clinico-pathological parameters.

| | Type | Grading | Max diameter (mm) | Positive LN (#) | ER | PR | Her2/Neu | Rab27B Protein (Score) | mRNA levels Normal | mRNA levels Tumor | FISH |
|---|---|---|---|---|---|---|---|---|---|---|---|
| 1 | IDCA | 3 | 25 | 2 | + | + | − | 2 | | | |
| 2 | IDCA | 2 | 7 | 0 | − | + | − | | | 0.55 | |
| 3 | IDCA | 2 | 18 | 3 | + | + | − | 1 | 3.82 | 8.78 | |
| 4 | Lob | 2 | 21 | 0 | + | − | − | 1 | | 9.59 | |
| 5 | IDCA | 2 | 11 | 0 | + | + | − | 1 | 0.85 | 9.42 | |
| 6 | IDCA | 3 | 21 | 0 | + | + | − | 2 | | 13.59 | No amplification |
| 7 | IDCA/DCIS | | 1 | 2 | − | − | +/− | 0 | | | |
| 8 | IDCA | 2 | 12 | 0 | + | + | − | 1 | 0.89 | 3.44 | |
| 9 | IDCA | 3 | 27 | 0 | + | + | − | 1 | | 9.53 | |
| 10 | DCIS | | | 1 | + | + | − | 2 | | 13.17 | No amplification |
| 11 | IDCA | 3 | 17 | 1 | + | + | − | 2 | | 34.5 | No amplification |
| 12 | IDCA | 3 | 12 | 0 | + | − | − | | | 15.17 | |
| 13 | IDCA | 3 | 20 | 1 | + | + | − | 2 | | | |
| 14 | IDCA | 2 | 10 | 0 | + | + | − | 2 | | | No amplification |
| 15 | IDCA | 3 | 19 | 0 | + | + | − | 1 | | | |
| 16 | IDCA | 3 | 54 | 1 | + | − | − | 2 | | | |
| 17 | IDCA | 2 | 9 | 0 | + | + | − | 1 | | | |
| 18 | IDCA | 3 | 18 | 1 | + | − | − | 1 | | | |
| 19 | IDCA | 3 | 35 | 0 | − | − | − | 0 | | 2.05 | |
| 20 | IDCA | 1 | 6 | 0 | + | + | − | 1 | | 17.54 | |
| 21 | IDCA | 3 | 8 | 0 | + | + | − | 1 | | | |
| 22 | Lob | | 18 | 0 | + | + | − | 1 | | | |
| 23 | IDCA | 3 | 22 | 2 | − | − | − | | | 5.79 | |
| 24 | IDCA | 3 | 24 | 1 | + | + | − | 2 | 0.82 | 58.17 | No amplification |
| 25 | IDCA | 3 | 9 | 4 | − | − | + | 0 | | | |
| 26 | IDCA | 1 | 10 | 1 | + | − | − | | 2.53 | 19.15 | |
| 27 | IDCA | 3 | 11 | 1 | − | − | − | 0 | | | |
| 28 | IDCA | 3 | 11 | 0 | + | + | − | 1 | | | |
| 29 | IDCA | 1 | 12 | 0 | + | + | − | 1 | | 10.26 | |
| 30 | IDCA | 3 | 8 | 0 | + | + | − | 1 | | | |

TABLE 1-continued

Tumor composition and Rab27B association with clinico-pathological parameters.

| | | | Max diameter | Positive LN | | | | Rab27B | | | |
| | | | | | | | | Protein | mRNA levels | | |
| | Type | Grading | (mm) | (#) | ER | PR | Her2/Neu | (Score) | Normal | Tumor | FISH |
|---|---|---|---|---|---|---|---|---|---|---|---|
| 31 | IDCA | 2 | 5 | 0 | + | + | − | 1 | | | |
| 32 | IDCA | 3 | 8 | 1 | − | − | + | 0 | | | |
| 33 | IDCA | 3 | 35 | 4 | − | − | + | 0 | | | |
| 34 | IDCA | 2 | 13 | 0 | + | + | − | 1 | | | |
| 35 | IDCA | 3 | 10 | 0 | + | + | − | 2 | | | No amplification |
| 36 | IDCA/Lob | 2 | 29 | 0 | + | + | − | 1 | | | |
| 37 | Lob | 2 | 75 | 0 | + | + | − | 1 | | 3.87 | |
| 38 | Lob | | 45 | 0 | + | + | − | 2 | | | |
| 39 | Lob | | 17 | 2 | + | + | − | 2 | | | |
| 40 | Lob | | 30 | 1 | + | − | − | 1 | | 17.8 | |
| 41 | Lob | | 32 | 2 | + | − | − | 2 | | | |
| 42 | Lob | | 40 | 12 | + | + | − | 1 | | | |
| 43 | IDCA | 3 | 35 | 2 | + | + | − | 2 | | | |
| 44 | IDCA | 2 | 13 | 1 | + | + | − | 2 | | | No amplification |
| 45 | IDCA | 3 | 22 | 0 | − | − | − | 0 | | | |
| 46 | IDCA | 3 | 10 | 3 | − | − | − | 0 | | 5.33 | |
| 47 | IDCA | 2 | 9 | 0 | + | + | − | 1 | | | |
| 48 | IDCA | 2 | 25 | 0 | + | + | − | 1 | | | |
| 49 | IDCA | 2 | 25 | 2 | + | + | − | 1 | | | |
| 50 | IDCA | 2 | 8 | 0 | + | + | − | 1 | | | |
| 51 | IDCA | 3 | 50 | 2 | − | − | − | 0 | | 5.73 | |
| 52 | IDCA | 2 | 8 | 0 | + | + | − | 1 | | | |
| 53 | IDCA | 3 | 17 | 1 | − | − | − | 0 | | | |
| 54 | IDCA | 3 | 9 | 2 | + | + | − | 1 | | | |
| 55 | IDCA | 2 | 30 | 6 | + | + | − | 2 | | | No amplification |
| 56 | IDCA | 2 | 11 | 0 | + | + | − | 1 | | | |
| 57 | IDCA | | 11 | | + | − | − | 1 | | | |
| 58 | Muc | 2 | 10 | 0 | + | + | − | 1 | | | |
| 59 | IDCA | 2 | 43 | | + | − | − | 1 | | | |
| 60 | DCIS/IDCA | | | 1 | + | + | − | 2 | | | No amplification |
| 61 | Lob | | 33 | 0 | + | + | − | 1 | | | |
| 62 | IDCA/DCIS | | 23 | 1 | + | − | − | 1 | | | |
| 63 | IDCA | 3 | 7 | 2 | + | − | − | 2 | | | No amplification |

Abbreviations:
DCIS: ductal breast carcinoma in situ;
ER: estrogen receptor;
IDCA: invasive ductal breast carcinoma;
LN: lymph node;
Lob: lobular breast carcinoma;
Muc: mucous breast carcinoma;
PR: progesteron receptor;
+: positive;
−: negative.

Taken together, the present invention discloses a new key mechanism linking the secretory small GTPase Rab27B with HSP90α secretion and leading to MMP-2 stabilization, activation and cancer cell invasion. It is shown that human breast cancer cells can recruit the Rab27B regulated secretory pathway to deliver pro-invasive signals involved in the degradation of extracellular matrix components. In addition to stimulating the reorganization of the actin cytoskeleton, the secretory Rab27B small GTPase can also induce G1/S cell cycle progression (FIG. 2). As a consequence, the present invention indicates that Rab27B promotes the invasive growth of primary tumors and the multiplication of peritoneal metastases established from MCF-7 human breast cancer xenografts (FIG. 3). The functional impact of the Rab27B small GTPase in vitro and in vivo depends exclusively upon lipid targeting (i.e., geranylgeranylation) and GTP binding (FIGS. 2 and 3). Moreover, the Rab27A isoform, which is structurally very similar to Rab27B and is a functional homologue with respect to melanosome transport (35) and which is critically involved in granule exocytosis in human neutrophils (34), does not mimick Rab27B!

Proteomic analysis of purified GFP-Rab27B vesicles and of the secretome of breast cancer cells expressing Rab27B identified HSP90α as a potential pro-invasive factor. The present invention shows that intracellular HSP90α, but not β, is secreted into the extracellular environment in a Rab27B-specific, GTP-dependent and geranylgeranyl-dependent manner (FIG. 4, A-C). Consistent with this finding, Rab27B siRNA targeting, as well as HSP90α neutralizing antibodies, pharmacological inhibitors and recombinant proteins demonstrated the critical role for Rab27B and HSP90α in enhancing breast cancer cell invasion (FIG. 4, D and FIG. 5, A-C). MMP-2 activation depends upon HSP90α secretion, and correlates with Rab27B activity (FIGS. 5, D and E). Hence, the present invention identified Rab27B expression as a key factor for the increased invasiveness, tumor size and metastasis of various ER-positive breast cancer cell lines, both in vitro and in vivo. Critically, in human breast cancer specimens the presence of Rab27B protein proved to be associated with a low degree of differentiation, lymph node metastasis and a positive ER-status (FIGS. 6, A and B). In agreement, levels of Rab27B mRNA were highest in ER-positive breast cancers with lymph node metastasis and lowest in ER-negative tumors (FIG. 6, C). Based on this body of evidence, Rab27B serves as a major effector of invasiveness and metastasis, and provides an important marker in the signature of ER-positive breast cancers with poor prognosis.

2. Rab27B-Targeting Compounds to Treat Estrogen-Positive Breast Cancer

Three types of compounds have capabilities to treat Rab27B positive poor prognosis estrogen-positive breast cancer, namely:

1) Genetic compounds such as Rab27B-specific small interfering RNA molecules (siRNAs) having as targets—within the nucleic acids encoding for Rab27B—for example the nucleic acid sequences 5' AAA CGT GTG GTT TAT AAT GCA 3' (SEQ ID NO:1) (siRab27B target 1) and 5' TAG GAA TAG ACT TTC GGG AAA 3' (SEQ ID NO:2) (siRab27B target 2). These siRNA compounds (50 nM) are electroporated in MCF-7 GFP-Rab27B breast cancer cells as described above.

2) Protein-peptide compounds such as the so-called 'Trojan peptides' containing a target sequence (see below) fused with the antennapedia peptide or other peptides (Gratton et al. (47)) or 'Alpha bodies' (www.complix.be) or 'nano bodies' (Van Impe et al. (51); Delanote et al. (45)) targeting functional domains of Rab27B such as the amino acid regions corresponding to the amino acids 42-56 (=VGIDFREKRV-VYNAQ (SEQ ID NO:3)), 55-69 AQGPNG SSGKAFKVH (SEQ ID NO:4), or, 79-93 ERFRSLTTAFFRDAM (SEQ ID NO:5), or targeting the Rab27B-specific 15AA C-terminal tail consisting of the amino acids GNSGNLDGEKPPEKK (SEQ ID NO:6). Trojan peptides are added to the culture medium of MCF-7 GFP-Rab27B breast cancer cells in concentrations ranging from 0.05 mM to 10 mM. A cDNA, encoding the $V_HH$ sequences of the nanobodies targeting the Rab27 functional domains, is subcloned in pcDNA3.1/V5-His-TOPO vector (Invitrogen) and overexpressed in MCF-7 GFP-Rab27B breast cancer cells.

To avoid Trojan peptide uptake by any cell in vivo, the Trojan peptide activity is temporally masked in the blood stream and later released near the targeted Rab27B positive breast cancer tissue. Such a strategy has been previously described with a poly-Arg peptide masked by a polyanionic peptide made with Asp and Glu residues (Jiang et al. (48)). It was shown in vitro and in vivo that under this form, the peptide was not able anymore to enter the cells, that the cleavage was specific of the MMP2 protease (MMP2 is also activated in Rab27B positive tumors; as described herein) and that this occurred mainly in the very close environment of the tumor. Therefore, a Trojan peptide linked to an inhibitory moiety through a linker sensitive to the secreted protease is designed. Since it is generally well-documented that the protease half-life is very short once released in the extracellular milieu, this instability leads in fact to its almost exclusive concentration in the close vicinity of the targeted cell type. Therefore, these strategies are used to selectively deliver Trojan peptides with Rab27B interfering activity into a targeted cell type 3) Small molecule compounds from the tetrahydrobenzodiazepine class, targeting Rab-geranylgeranylation (BMS1, BMS2 or BMS3) as described in detail in ref. 39. Geranylgeranyl transferase prenylates exclusively the GTPases of Rab family, and inhibition of this enzyme induces apoptosis in cancer cells and inhibits poor prognosis ER-positive tumors. The doses for in vitro use range between 0.1 and 10 µM. Doses for in vivo use range between 10-75 mg/kg.

A cellular analysis is performed to assess a functional role of Rab27B targeted therapy. It is established that untreated cultured cells show a peripheral distribution of GFP-Rab27B positive vesicles (as described herein). Perturbation of peripheral vesicle localization inhibits secretion of vesicle content and therefore invasion. Quantification of peripheral and perinuclear vesicular distribution of GFP-Rab27B positive vesicles in treated versus non-treated cells is quantified by laser scanning confocal microscopy, combined with an actin-stain and DAPI stain to visualize the cell boundaries and nucleus, respectively. To analyse GFP-Rab27B distribution, the total area containing GFP-Rab27B vesicles is outlined with a solid line, and 75% of the area surrounded by the solid line is indicated by a broken red line. We define the cell periphery as the outermost 25% of the cell area (exemplified in Kuroda and Fukuda (49)). The total GFP signals in a single cell and the GFP signals in the peripheral part of the cell are quantified, and the percentage of peripheral GFP-Rab27B vesicles, that is, GFP-Rab27B vesicles present in the outermost 25% of the cell area are calculated. More than 60 randomly selected cells (more than 20 cells per dish, three independent dishes for each condition) are examined. Data are expressed by box- and whisker plots as means±95% confidence intervals of three independent experiments and are analysed by Student's t-test. It is known that Rab27B interacts directly with several of its effector proteins and indirectly with actin-associated motor proteins (Fukuda (46)). Re-distribution of secretory vesicles towards the perinuclear area often indicate a perturbation of the binding between the rab and its effector and/or motor protein. GFP-Rab27B-effector association is analysed in treated versus non-treated cells by biochemical co-immunoprecipitation assays followed by western blotting (Kuroda and Fukuda (49)). It has been established that secretion of HSP90 alpha is Rab27B-dependent and that HSP90 alpha is a key pro-invasive factor in the Rab27B-dependent invasion process (as described herein), measurement of secreted HSP90 alpha with ELISA in conditioned medium of treated versus non-treated cells is an indicator of Rab27B-dependent secretion.

The functional role of the Rab27B-targeting compounds in invasion and metastasis is studied using well known techniques such as Matrigel- and native collagen type I invasion assays, morphometry, and growth curve- and cell cycle analysis as described in detail in De Wever et al. (44); Albini and Benelli (43); Ahmed et al. (42)). Local invasive growth and peritoneal metastasis formation is analysed in a Swiss nu/nu orthotopic mouse model. Female mice are primed with an estradiol pellet and one week later the mammary fat pad is prepared by injecting $10^6$ MCF-7 GFP-Rab27B breast cancer cells engineered to express the Rab27B-targeted compounds as described above. Alternatively, mice with orthotopically injected MCF-7 GFP-Rab27B breast cancer cells receive bi-weekly intraperitoneal injection of geranylgeranyl transferase inhibitor BMS1, BMS2 or BMS3 (Lackner et al., 2005) in doses as indicated above. Tumor volume is estimated by using the equation, $V=0.4 \times a \times b^2$, where 'V' is volume, 'a' is the length of the major axis of the tumor, and 'b' is the length of its minor axis. Intraperitoneal metastasis formation is assessed weekly via palpation and visual analysis of the blue and swollen appearance of the abdomen. Mouse survival time is defined as the time from injection until the animals died or were euthanized by cervical dislocation when the abdominal circumference increased 60% above normal controls.

Kaplan-Meier curves and log-rank testing are used for survival analyses. For tumor weights, comparisons are performed using a two-sided unpaired Student's t-test following D'Agostino-Pearson testing for normal distribution.

REFERENCES

1. Comoglio P M, Trusolino L. Invasive growth: from development to metastasis. *J Clin Invest.* 2002; 109(7):857-862.

2. Palmer R E, Lee S B, Wong J C, et al. Induction of BAIAP3 by the EWS-WT1 chimeric fusion implicates regulated exocytosis in tumorigenesis. *Cancer Cell.* 2002; 2(6):497-505.
3. Pereira-Leal J B, Seabra M C. Evolution of the Rab family of small GTP-binding proteins. *J Mol Biol.* 2001; 313(4): 889-901.
4. Zerial M, McBride H. Rab proteins as membrane organizers. *Nat Rev Mol Cell Biol.* 2001; 2(3):107-117.
5. Vetter I R, Wittinghofer A. The guanine nucleotide-binding switch in three dimensions. *Science.* 2001; 294(5545): 1299-1304.
6. Pfeffer S R. Structural clues to Rab GTPase functional diversity. *J Biol Chem.* 2005; 280(16):15485-15488.
7. Leung K F, Baron R, Seabra M C. Thematic review series: lipid posttranslational modifications. Geranylgeranylation of Rab GTPases. *J Lipid Res.* 2006; 47(3):467-475.
8. Burgess T L, Kelly R B. Constitutive and regulated secretion of proteins. *Annu Rev Cell Biol.* 1987; 3:243-293.
9. Chavez R A, Miller S G, Moore H-P H. A biosynthetic regulated secretory pathway in constitutive secretory cells. *J Cell Biol.* 1996; 133(6):1177-1191.
10. Burgoyne R D, Morgan A. Secretory granule exocytosis. *Physiol Rev.* 2003; 83(2):581-632.
11. Fukuda M. Regulation of secretory vesicle traffic by Rab small GTPases. *Cell Mol Life Sci.* 2008; 65(18):2801-2813.
12. Nashida T, Imai A, Shimomura H. Relation of Rab26 to the amylase release from rat parotid acinar cells. *Arch Oral Biol.* 2006; 51(2):89-95.
13. Masuda E S, Luo Y, Young C, et al. Rab37 is a novel mast cell specific GTPase localized to secretory granules. *FEBS Lett.* 2000; 470(1):61-64.
14. Takai Y, Sasaki T, Shirataki H, Nakanishi H. Rab3A small GTP-binding protein in Ca(2+)-dependent exocytosis. *Genes Cells.* 1996; 1(7): 615-632.
15. Gomi H, Mori K, Itohara S, Izumi T. Rab27b is expressed in a wide range of exocytic cells and involved in the delivery of secretory granules near the plasma membrane. *Mol Biol Cell.* 2007; 18(11):4377-4386.
16. Tolmachova T, Anders R, Stinchcombe J, et al. A general role for Rab27a in secretory cells. *Mol Biol Cell.* 2004; 15(1):332-344.
17. Chen D, Guo J, Miki T, Tachibana M, Gahl W A. Molecular cloning and characterization of rab27a and rab27b, novel human rab proteins shared by melanocytes and platelets. *Biochem Mol Med.* 1997; 60(1):27-37.
18. Cheng K W, Lahad J P, Kuo W-1, et al. The RAB25 small GTPase determines aggressiveness of ovarian and breast cancers. *Nat Med.* 2004; 10(11): 1251-1256.
19. Liu Y-J, Wang Q, Li W, et al. Rab23 is a potential biological target for treating hepatocellular carcinoma. *World J Gastroenterol.* 2007; 13(7):1010-1017.
20. Hou Q, Wu Y H, Grabsch H, et al. Integrative genomics identifies RAB23 as an invasion mediator gene in diffuse-type gastric cancer. *Cancer Res.* 2008; 68(12):4623-4630.
21. Fukui K, Tamura S, Wada A, et al. Expression of Rab5a in hepatocellular carcinoma: possible involvement in epidermal growth factor signaling. *Hepatol Res.* 2007; 37(11): 957-965.
22. Bravo-Cordero J J, Marrero-Diaz R, Megias D, et al. MT1-MMP proinvasive activity is regulated by a novel Rab8-dependent exocytic pathway. *EMBO J.* 2007; 26(6): 1499-1510.
23. Neve R M, Chin K, Fridlyand J, et al. A collection of breast cancer cell lines for the study of functionally distinct cancer subtypes. *Cancer Cell.* 2006; 10(6):515-527.
24. Barral D C, Ramalho J S, Anders R, et al. Functional redundancy of Rab27 proteins and the pathogenesis of Griscelli syndrome. *J Clin Invest.* 2002; 110(2):247-257.
25. Maynard D M, Heijnen H F G, Home M K, White J G, Gahl W A. Proteomic analysis of platelet α-granules using mass spectrometry. *J Thromb Haemost.* 2007; 5(9):1945-1955.
26. Perkins D N, Pappin D J, Creasy D M, Cottrell J S. Probability-based protein identification by searching sequence databases using mass spectrometry data. *Electrophoresis.* 1999; 20(18):3551-3567.
27. De Wever O, Nguyen Q-D, Van Hoorde L, et al. Tenascin-C and SF/HGF produced by myofibroblasts in vitro provide convergent pro-invasive signals to human colon cancer cells through RhoA and Rac. *FASEB J.* 2004; 18(9): 1016-1018.
28. Pinner S, Sahai E. PDK1 regulates cancer cell motility by antagonising inhibition of ROCK1 by RhoE. *Nat Cell Biol.* 2008; 10(2):127-137.
29. Denys H, Derycke L, Hendrix A, et al. Differential impact of TGF-β and EGF on fibroblast differentiation and invasion reciprocally promotes colon cancer cell invasion. *Cancer Lett.* 2008; 266(2):263-274.
30. McNeill R E, Miller N, Kerin M J. Evaluation and validation of candidate endogenous control genes for real-time quantitative PCR studies of breast cancer. *BMC Mol Biol.* 2007; 8:107.
31. Eustace B K, Sakurai T, Stewart J K, et al. Functional proteomic screens reveal an essential extracellular role for hsp90α in cancer cell invasiveness. *Nat Cell Biol.* 2004; 6(6):507-514.
32. Sharp S, Workman P. Inhibitors of the HSP90 molecular chaperone: current status. *Adv Cancer Res.* 2006; 95:323-348.
33. Mosesson Y, Mills G B, Yarden Y. Derailed endocytosis: an emerging feature of cancer. *Nat Rev Cancer.* 2008; 8(11):835-850.
34. Herrero-Turrion M J, Calafat J, Janssen H, Fukuda M, Mollinedo F. Rab27a regulates exocytosis of tertiary and specific granules in human neutrophils. *J Immunol.* 2008; 181(6):3793-3803.
35. Westbroek W, Lambert J, De Schepper S, et al. Rab27b is up-regulated in human Griscelli syndrome type II melanocytes and linked to the actin cytoskeleton via exon F-Myosin Va transcripts. *Pigment Cell Res.* 2004; 17(5):498-505.
36. Wang J-S, Wang F-B, Zhang Q-G, Shen Z-Z, Shao Z-M. Enhanced expression of Rab27A gene by breast cancer cells promoting invasiveness and the metastasis potential by secretion of insulin-like growth factor-II. *Mol Cancer Res.* 2008; 6(3):372-382.
37. Pagani O, Price K N, Gelber R D, et al. Patterns of recurrence of early breast cancer according to estrogen receptor status: a therapeutic target for a quarter of a century. *Breast Cancer Res Treat.* 2009; doi: 10.1007/s10549-008-0282-0.
38. Bloom H, Richardson W (1957). "Histological grading and prognosis in breast cancer; a study of 1409 cases of which 359 have been followed for 15 years" *Br J Cancer* 11 (3): 359-77.
39. Lackner M R, Kindt R M, Carroll P M, Brown K, Cancilla M R, Chen C, de Silva H, Franke Y, Guan B, Heuer T, Hung T, Keegan K, Lee J M, Manne V, O'Brien C, Parry D, Perez-Villar J J, Reddy R K, Xiao H, Zhan H, Cockett M, Plowman G, Fitzgerald K, Costa M, Ross-Macdonald P. Chemical genetics identifies Rab geranylgeranyl transferase as an apoptotic target of farnesyl transferase inhibitors. Cancer Cell. 7:325-36, 2005

40. Hendrix A. et al. New insights in the link between Rab27b GTPase and breast cancer. Mol. Biol. Cell Vol 17 (supp) 2006, Abstract No 169.
41. Wright et al. Estrogen regulates vesicle trafficking gene expression in EFF-3, EFM-19 and MCF-7 breast cancer cells. Int J Clin Exp Pathol 2009: 463-475.
42. Ahmed A U, Schmidt R L, Park C H, Reed N R, Hesse S E, Thomas C F, Molina J R, Deschamps C, Yang P, Aubry M C, Tang A H. Effect of disrupting seven-in-absentia homolog 2 function on lung cancer cell growth. J Natl Cancer Inst. 2008 Nov. 19; 100(22): 1606-29.
43. Albini A, Benelli R. The chemoinvasion assay: a method to assess tumor and endothelial cell invasion and its modulation. Nat Protoc. 2007; 2(3):504-11.
44. De Wever O, Hendrix A, De Boeck A, Westbroek W, Braems G, Emami S, Sabbah M, Gespach C, Bracke M. Modeling and quantification of cancer cell invasion through collagen type I matrices. Int J Dev Biol. 2010; 54(5):887-96
45. Delanote V, Vanloo B, Catillon M, Friederich E, Vandekerckhove J, Gettemans J. An alpaca single-domain antibody blocks filopodia formation by obstructing L-plastin-mediated F-actin bundling. FASEB J. 2010 January; 24(1): 105-18.
46. Fukuda M. Versatile role of Rab27 in membrane trafficking: focus on the Rab27 effector families. J Biochem. 2005 January; 137(1):9-16.
47. Gratton J P, Yu J, Griffith J W, Babbitt R W, Scotland R S, Hickey R, Giordano F J, Sessa W C. Cell-permeable peptides improve cellular uptake and therapeutic gene delivery of replication-deficient viruses in cells and in vivo. Nat Med. 2003 March; 9(3):357-62.
48. Jiang T, Olson E S, Nguyen Q T, Roy M, Jennings P A, Tsien R Y. Tumor imaging by means of proteolytic activation of cell-penetrating peptides. Proc Natl Acad Sci USA. 2004 Dec. 21; 101(51):17867-72.
49. Kuroda T S, Fukuda M. Rab27A-binding protein Slp2-a is required for peripheral melanosome distribution and elongated cell shape in melanocytes. Nat Cell Biol. 2004 December; 6(12):1195-203.
50. Nguyen Q T, Olson E S, Aguilera T A, Jiang T, Scadeng M, Ellies L G, Tsien R Y. Surgery with molecular fluorescence imaging using activatable cell-penetrating peptides decreases residual cancer and improves survival. Proc Natl Acad Sci USA. 2010 Mar. 2; 107(9):4317-22.
51. Van Impe K, Hubert T, De Corte V, Vanloo B, Boucherie C, Vandekerckhove J, Gettemans J. A new role for nuclear transport factor 2 and Ran: nuclear import of CapG. Traffic. 2008 May; 9(5):695-707.

The invention claimed is:

1. A method of treating a subject for poor prognosis estrogen receptor-positive breast cancer, the method comprising:
treating a subject determined to be suffering from poor prognosis estrogen receptor-positive breast cancer by a diagnostic method comprising:
determining the level of guanosine triphosphate hydrolaze Rat brain (Rab) 27B in a sample from the subject;
comparing the level of Rab27B in the sample to a level of Rab27B in a control sample from someone having estrogen receptor-positive breast cancer without lymph-node metastasis, and
determining that the subject is suffering from poor prognosis estrogen receptor-positive breast cancer where there is an increased level of Rab27B in the sample as compared to the control sample,
wherein the treatment of the subject is selected form the group consisting of administering to the subject an HSP90α inhibitor, a compound which decreases the mRNA expression of Rab27B or the biological activity of Rab27B protein in the subject, and any combination thereof.

2. The method according to claim 1, wherein said poor prognosis corresponds with positive lymph node metastasis and/or a poor differentiation grade.

3. The method according to claim 1, wherein the level of Rab27B is determined by measuring the level of Rab27B protein or the level of Rab27B mRNA.

4. The method according to claim 1, wherein an increased level of Rab27B is indicated by more than 30% of cancer cells in the sample from the subject showing Rab27B protein membrane localization and/or vesicle clustering.

5. The method according to claim 1 wherein an increased level of Rab27B is indicated by a significantly higher level of Rab27B mRNA in the sample from the subject as compared to the control sample.

6. The method according to claim 1, wherein determining the level of Rab27B is determined with a kit comprising reagents to perform an assay for measuring Rab27B levels in a sample from a subject having estrogen receptor-positive breast cancer.

7. The method according to claim 6 wherein said assay is a Rab27B immunohistochemistry assay, a Quantitative RT-PCR assay, or a sandwich-type ELISA assay.

8. The method according to claim 1, wherein the compound is selected from the group consisting of an antibody, a peptide, a peptidomimetic, a small molecule, a nucleic acid, a Rab27B-specific small interfering RNA molecule, a peptide targeting a functional domain of Rab27B or targeting a Rab27B-specific domain, and a small molecule inhibiting the enzymatic activity of geranylgeranyltransferases.

9. The method according to claim 1, wherein the compound is selected from the group consisting of administering a Rab27B-specific small interfering RNA molecule that targets Rab27B nucleic acid sequence SEQ ID NO:1, a peptide targets one of the Rab27B functional amino acid domains SEQ ID NO:3, SEQ ID NO:4 or SEQ ID NO:5 and a peptide that targets the Rab27B-specific 15 amino acid C-terminal tail consisting of SEQ ID NO:6.

10. The method according to claim 1, wherein the HSP90α inhibitor is selected from the group consisting of a HSP90a neutralizing antibody and a pharmacological inhibitor.

11. The method according to claim 1, wherein the compound is a Rab27B-specific small interfering RNA molecule that targets the Rab27B nucleic acid sequence SEQ ID NO:1.

* * * * *